(12) United States Patent
Breslow et al.

(10) Patent No.: US 9,890,136 B2
(45) Date of Patent: Feb. 13, 2018

(54) SELECTIVE HDAC6 INHIBITORS

(71) Applicants: Ronald Breslow, New York, NY (US); Paul Marks, Washington, CT (US); Adaickapillai Mahendran, Brooklyn, NY (US); Yuanshan Yao, Shanghai (CN)

(72) Inventors: Ronald Breslow, New York, NY (US); Paul Marks, Washington, CT (US); Adaickapillai Mahendran, Brooklyn, NY (US); Yuanshan Yao, Shanghai (CN)

(73) Assignee: THE TRUSTEES OF COLUMBIA UNIVERSITY IN THE CITY OF NEW YORK MEMORIAL SLOAN-KETTERING CANCER CENTER, New York, NY (US)

( * ) Notice: Subject to any disclaimer, the term of this patent is extended or adjusted under 35 U.S.C. 154(b) by 0 days.

(21) Appl. No.: 15/107,272

(22) PCT Filed: Dec. 23, 2014

(86) PCT No.: PCT/US2014/072234
§ 371 (c)(1),
(2) Date: Jun. 22, 2016

(87) PCT Pub. No.: WO2015/100363
PCT Pub. Date: Jul. 2, 2015

(65) Prior Publication Data
US 2016/0347732 A1 Dec. 1, 2016

Related U.S. Application Data

(60) Provisional application No. 61/920,307, filed on Dec. 23, 2013.

(51) Int. Cl.
*C07C 233/69* (2006.01)
*A61K 31/166* (2006.01)
(Continued)

(52) U.S. Cl.
CPC .......... *C07D 333/38* (2013.01); *A61K 31/166* (2013.01); *A61K 31/216* (2013.01);
(Continued)

(58) Field of Classification Search
CPC ... C07D 333/38; C07C 233/65; C07C 233/69; C07C 237/42; C07C 259/10
(Continued)

(56) References Cited

U.S. PATENT DOCUMENTS 4,309,212 A  1/1982  Takemoto et al.
5,369,108 A  11/1994  Breslow et al.
(Continued)

FOREIGN PATENT DOCUMENTS

EP  0434074 A2  6/1991
EP  1736465 A1  12/2006
(Continued)

OTHER PUBLICATIONS

Chemical Abstracts STN Registry database record for RN 1249139-98-7, entered on Oct. 31, 2010.*
(Continued)

*Primary Examiner* — Daniel Carcanague
(74) *Attorney, Agent, or Firm* — John P. White; Cooper & Dunham LLP

(57) ABSTRACT

The present invention provides a compound having the structure:
(Continued)

- A structurally and functionally unique member of the HDAC family
- Localized to the cytoplasm
- Deacetylates a number of non-histone proteins including Hsp90, α-tubulin, Peroxiredoxin etc. Histones are not substrates for HDAC6
- Two catalytic domains
- Intrinsic ubiquitin- and dynein-binding activity

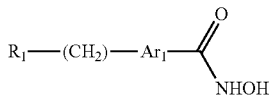

wherein
$R_1$ is halogen, $-NR_5R_6$, $-NR_5-C(=O)-R_6$, $-NH-C(=O)-OR_7$, $-OR_7$, $-NO_2$, $-CN$, $-SR_7$, $-SO_2R_7$, $-CO_2R_7$, $CF_3$, $-SOR_7$, $-POR_7$, $-C(=S)R_7$, $-C(=O)-NR_5R_6$, $-CH_2-C(=O)-NR_5R_6$, $-C(=NR_5)R_6$, $-P(=O)(OR_5)(OR_6)$, $-P(OR_5)(OR_6)$, $-C(=S)R_7$, $C_{1-5}$ alkyl, $C_{2-5}$ alkenyl, $C_{2-5}$ alkynyl, aryl, heteroaryl, or heterocyclyl, wherein $R_5$, $R_6$, and $R_7$ and are each, independently, H, $C_{1-5}$ alkyl, $C_{2-5}$ alkenyl, $C_{2-5}$ alkynyl, heteroalkyl, hydroxyalkyl, cycloalkyl, heterocycloalkyl, aryl, heteroaryl, $C_{1-5}$ alkyl-aryl, or $C_{1-5}$ alkyl-NH-aryl;

$Ar_1$ is phenyl or thiophene;

wherein when $Ar_1$ is phenyl, then $R_1$ is other than $-C(=O)-NR_5R_6$, where one of $R_5$ or $R_6$ is phenyl or quinoline and the other of $R_5$ or $R_6$ is hydroxyalkyl, or where one of $R_5$ or $R_6$ is quinoline and the other of $R_5$ or $R_6$ is H; and wherein when $Ar_1$ is phenyl, then $R_1$ is other than $-NR_5-C(=O)-R_6$, where one of $R_5$ is H and $R_6$ is quinoline, or a pharmaceutically acceptable salt thereof.

22 Claims, 7 Drawing Sheets

(51) Int. Cl.

| | | |
|---|---|---|
| C07C 233/65 | (2006.01) | |
| A61K 31/381 | (2006.01) | |
| A61K 45/06 | (2006.01) | |
| C07C 237/42 | (2006.01) | |
| A61K 31/216 | (2006.01) | |
| C07D 333/38 | (2006.01) | |
| C07C 259/10 | (2006.01) | |

(52) U.S. Cl.
CPC ............ *A61K 31/381* (2013.01); *A61K 45/06* (2013.01); *C07C 233/65* (2013.01); *C07C 233/69* (2013.01); *C07C 237/42* (2013.01); *C07C 259/10* (2013.01)

(58) Field of Classification Search
USPC ........................................................ 549/70
See application file for complete search history.

(56) References Cited

U.S. PATENT DOCUMENTS

| | | | |
|---|---|---|---|
| 5,932,616 | A | 8/1999 | Breslow et al. |
| 7,282,522 | B2 | 10/2007 | Rho et al. |
| 7,345,174 | B2 | 3/2008 | Breslow et al. |
| 9,499,479 | B2 | 11/2016 | Breslow et al. |
| 2004/0087631 | A1 | 5/2004 | Bacopoulos et al. |
| 2004/0122079 | A1 | 6/2004 | Grossmann et al. |
| 2005/0119305 | A1 | 6/2005 | Naka et al. |
| 2006/0241129 | A1 | 10/2006 | Breslow et al. |
| 2006/0252834 | A1 | 11/2006 | Rho et al. |
| 2007/0010669 | A1 | 1/2007 | Breslow et al. |
| 2007/0213392 | A1 | 9/2007 | Miller et al. |
| 2008/0139673 | A1 | 6/2008 | Hu et al. |
| 2008/0200489 | A1 | 8/2008 | Atadja et al. |
| 2008/0248506 | A1 | 10/2008 | Bass et al. |
| 2009/0023786 | A1 | 1/2009 | Miller et al. |
| 2010/0022514 | A1 | 1/2010 | Cho et al. |
| 2011/0212943 | A1 | 9/2011 | Balasubramanian et al. |
| 2014/0031368 | A1 | 1/2014 | Breslow et al. |
| 2014/0288119 | A1 | 9/2014 | Breslow et al. |
| 2017/0066712 | A1* | 3/2017 | Breslow ............... C07C 259/06 |

FOREIGN PATENT DOCUMENTS

| | | |
|---|---|---|
| EP | 2045239 A1 | 4/2009 |
| WO | WO 02/26696 A1 | 4/2002 |
| WO | WO 2005/055928 A1 | 6/2005 |
| WO | WO 2005/080367 A1 | 9/2005 |
| WO | WO 2006/101454 A1 | 9/2006 |
| WO | WO 2006/117548 A1 | 11/2006 |
| WO | WO 2007/124435 A2 | 11/2007 |
| WO | WO 2008/055068 A1 | 5/2008 |
| WO | WO 2011/011186 A1 | 1/2011 |
| WO | WO 2011/146855 A1 | 9/2011 |
| WO | WO 2013/052110 A1 | 4/2013 |

OTHER PUBLICATIONS

Chemical Abstracts STN Registry database record for RN 1027592-42-2, entered on Jun. 12, 2008.*
Bergman; Journal of Medicinal Chemistry 2012, 55, 9891-9899.*
Gryder; Future Med Chem. 2012, 4, 505-524.*
Inks; ACS Chem. Biol. 2012, 331-339.*
Lee; PNAS 2015, 112, 12005-12010.*
Santo; Blood 2012, 119, 2579-2589.*
International Search Report in connection with PCT International Application No. PCT/US2014/072234, dated Mar. 18, 2015.
Written Opinion of the International Searching Authority in connection with PCT International Application No. PCT/US2014/072234, dated Mar. 18, 2015.
International Search Report in connection with PCT International Application No. PCT/US2011/037372 dated Aug. 17, 2011.
International Preliminary Report on Patentability Chapter I in connection with PCT International Application No. PCT/US2011/037372 dated Nov. 27, 2012.
Written Opinion of the International Search Authority in connection with PCT International Application No. PCT/US2011/037372 dated Aug. 17, 2011.
Office Action dated Mar. 18, 2014 in connection with U.S. Appl. No. 13/937,128.
Office Action dated Aug. 7, 2014 in connection with U.S. Appl. No. 13/937,128.
Final Office Action dated Jan. 28, 2015 in connection with U.S. Appl. No. 13/937,128.
Office Action dated Aug. 21, 2015 in connection with U.S. Appl. No. 13/937,128.
Supplementary European Search Report dated Aug. 20, 2014 in connection with European Application No. 11784333.4.
Communication Pursuant to 94(3) EPC dated Aug. 5, 2015 in connection with European Application No. 11784333.4.
Office Action dated Sep. 4, 2015 in connection with Australian Patent Application No. 2011255281.
Written Opinion of the International Search Authority in connection with PCT International Application No. PCT/US2012/000459 dated Dec. 11, 2012.
International Preliminary Report on Patentability Chapter I in connection with PCT International Application No. PCT/US2012/000459 dated Apr. 17, 2014.
International Search Report in connection with PCT International Application No. PCT/US2012/000459 dated Dec. 11, 2012.
Office Action dated Dec. 17, 2014 in connection with U.S. Appl. No. 14/349,291.
Office Action dated Jun. 26, 2015 in connection with U.S. Appl. No. 14/349,291.
Office Action dated Nov. 4, 2015 in connection with U.S. Appl. No. 14/349,291.
Notice of Allowance dated Aug. 24, 2016 in connection with U.S. Appl. No. 14/349,291.

(56) References Cited

OTHER PUBLICATIONS

Invitation Pursuant to Rule 63(1) EPC dated Jun. 26, 2015 in connection with European Application No. 12838935.0.
Extended European Search Report dated Oct. 20, 2015 in connection with European Application No. 12838935.0.
Office Action dated Nov. 13, 2015 in connection with Australian Patent Application No. 2012319188.
Office Action dated Jul. 15, 2016 in connection with Australian Patent Application No. 2012319188.
Office Action dated Oct. 25, 2016 in connection with Australian Patent Application No. 2012319188.
International Preliminary Report on Patentability Chapter I in connection with PCT International Application No. PCT/US2014/072234 dated Mar. 18, 2015.
Siliphaivanh, P, et al. Design of novel histone deacetylase inhibitors. Bioorg Med Chem Lett. (2007), 17(16), pp. 4619-4624.
Estiu, et al. Structural origin of selectivity in class II-selective histone deacetylase inhibitors. J Med Chem. (2008), 51(10), pp. 2898-2906.
R. B. Parmigiani et al. HDAC6 is a specific deacetylase of peroxiredoxins and is involved in redox regulation. PNAS (2008), 105(28), pp. 9633-9638.
Bieliauskas, A.V. and Pflum, M.K. Isoform-selective histone deacetylase inhibitors. Chem Soc Rev. (2008), 37(7), pp. 1402-1413.
Belvedere, S. et al. Aminosuberoyl hydroxamic acids (ASHAs): a potent new class of HDAC inhibitors. Bioorg Med Chem Lett. (2007), 17(14), 3969-71.
Bali, P. et al. Inhibition of Histone Deacetylase 6 Acetylates and Disrupts the Chaperone Function of Heat Shock Protein 90. Journal of Biological Chemistry. (2005), 280, pp. 26729-26734.
Gao et al. The Microtubule-associated Histone Deacetylase 6 (HDAC6) Regulates Epidermal Growth Factor Receptor (EGFR) Endocytic Trafficking and Degradation. Journal of Biological Chemistry. (2010), 285, pp. 11219-11226.
Kovacs, J.J. et al. HDAC6 Regulates Hsp90 Acetylation Short Article and Chaperone-Dependent Activation of Glucocorticoid Receptor. Molecular Cell. (2005), 18, pp. 601-607.
Haggarty, S.J. et al. Domain-selective small-molecule inhibitor of histone deacetylase 6 (HDAC6)-mediated tubulin deacetylation. PNAS (2003), 100, pp. 4389-4394.
Butler, K.V. et al. Chemical Origins of Isoform Selectivity in Histone Deacetylase Inhibitors. Current Pharmaceutical Design. (2008) 14, pp. 505-528.
Kawaguchi, Y. et al.The Deacetylase HDAC6 Regulates Aggresome Formation and Cell Viability in Response to Misfolded Protein Stress. (2003) Cell, vol. 115, 727-738.
Kozikowski, A.P. et al. Use of the nitrile oxide cycloaddition (NOC) reaction for molecular probe generation: a new class of enzyme selective histone deacetylase inhibitors (HDACIs) showing picomolar activity at HDAC6. J. Med. Chem. (2008) 51, 4370-7373.
Hong, J. et al. A New Approach to Tubacin. Letters in Organic Chemistry. (2010) 7, 50-53.
Griffith, D. A novel anti-cancer bifunctional platinum drug candidate with dual DNA binding and histone deacetylase inhibitory activity. Chem Commun (Camb). (2009) 28, 44, 6735-7.
CAS Abstract for Canonica & Tedechi, 13 Farmaco, Edizione Scientiifca (1958), 286-93.
CAS Abstract for JP 510014124, published Apr. 18, 1974 (Harita et al.).
Uesato, S. et al. Novel histone deacetylase inhibitors: N-hydroxycarboxamides possessing a terminal bicyclic aryl group. Bioorg. Med. Chem. Lett. (2002) 12, 1347-1349.
Maeda, T. et al. Potent histone deacetylase inhibitors: N-hydroxybenzamides with antitumor activities. Bioorg. Med. Chem. (2004) 12, 4351-4360.
Butler et al. Rational Design and Simple Chemistry Yield a Superior, Neuroprotective HDAC6 Inhibitor, Tubastatin A. J. Am. Chem. Soc. (2010) 132, 10842-10846.
Smil, D.V. et al. Novel HDAC6 isoform selective chiral small molecule histone deacetylase inhibitors. Bioorg. Med. Chem. Lett. (2009) 19, 688-692.
Marastoni, E. et al. Benzofused hydroxamic acids: Useful fragments for the preparation of histone deacetylase inhibitors. Part 1: Hit identification. Bioorg. Med. Chem. Lett. (2013) 23, 4091-4095.
Lee, J. et al. Development of a histone deacetylase 6 inhibitor and its biological effects PNAS (2013) 110, 15704-15709.
Office Action dated Apr. 10, 2017 in connection with European Patent Application No. 12838935.0.

\* cited by examiner

- A structurally and functionally unique member of the HDAC family
- Localized to the cytoplasm
- Deacetylates a number of non-histone proteins including Hsp90, $\alpha$-tubulin, Peroxiredoxin etc. Histones are not substrates for HDAC6
- Two catalytic domains
- Intrinsic ubiquitin- and dynein-binding activity

SELECTIVE HDAC6 INHIBITORS

CROSS-REFERENCE TO RELATED APPLICATIONS

This application is a § 371 national stage of PCT International Application No. PCT/US2014/072234, filed Dec. 23, 2014, claiming the benefit of U.S. Provisional Application No. 61/920,307, filed Dec. 23, 2013, the content of each of which is hereby incorporated by reference into the application.

Throughout this application, certain publications are referenced in parentheses. Full citations for these publications may be found immediately preceding the claims. The disclosures of these publications in their entireties are hereby incorporated by reference into this application in order to describe more fully the state of the art to which this invention relates.

BACKGROUND OF THE INVENTION

To date, eighteen histone deacetylases (HDACs) have been identified in humans. Eleven HDACs (HDAC1-11) are zinc-dependent and seven HDACs, designated sirtuins 1-7, are NAD$^+$-dependent (Parmigiani, R. B. et al. 2008). Aberrant activity of HDACs has been implicated in many disease states, including cancer (Butler, K. V. et al. 2008). When zinc-dependent HDACs are inhibited, the levels of acetylation of certain proteins are elevated, with many resulting physiological effects. Many inhibitors of HDACs have been developed for use against cancers and other disease states. One well-known HDAC inhibitor, suberoylanilide hydroxamic acid (SAHA, Vorinostat), was approved in 2006 for human use following the results of more than 100 human trials against various forms of cancer and is currently in use. Phase I, II and III clinical trials with vorinostat as single therapy and in combination therapy with various anti-cancer agents for hematologic and solid neoplasms are ongoing.

While HDACs are associated with deacetylation of histones in the context of gene expression and chromatin remodeling, there is abundant evidence indicating that not all functions of HDACs are dedicated to deacetylation of histones. Rather, some HDACs have been shown to exert deacetylase activity on proteins other than histones. One such HDAC is HDAC6, a cytoplasmic, microtubule-associated deacetylase, which has been found to regulate microtubule acetylation and chemotactic cell motility (Kawaguchi, Y. et al. 2003).

HDAC6 is predominantly a cytoplasmic, microtubule-associated member of the class IIB family of histone deacetylases. HDAC6 possesses two catalytic domains, a ubiquitin-binding domain and a C-terminal zinc finger domain (Bali, P. et al. 2005). HDAC6 catalyzes deacetylation of cytoplasmic protein substrates, such as α-tubulin, Hsp90, peroxiredoxins, and cortactin (Bali, P. et al. 2005). HDAC6 has also been demonstrated to direct misfolded protein aggregates into aggresomes, which are major repositories formed to manage excessive levels of misfolded and aggregated protein for eventual elimination. Aggresomes are of clinical interest as they are similar to cytoplasmic inclusion bodies commonly observed in neurodegenerative diseases (Gao, Y.-S. et al. 2010).

It has been shown that the C-terminal catalytic domain of HDAC6, the domain responsible for α-tubulin deacetylation, can be inhibited by the small-molecule inhibitor, tubacin (Haggarty, S. J. et al. 2003). Haggarty et al found that the inhibition of HDAC6 with tubacin did not affect the stability of microtubules, but decreased cell motility. Given the dependence of metastasis and angiogenesis on cell movement, increasing the acetylation level of α-tubulin may be an important component to the antimetastatic and anti-angiogenic activities of HDAC inhibitors (Haggarty, S. J. et al. 2003).

Heat shock protein 90 (Hsp90) is an important chaperone protein involved in protein folding and is overexpressed in many cancer cell types (Butler, K. V. et al. 2008; Kovacs, J. J. et al. 2005). The disruption of the folding and chaperoning functions of Hsp90 causes its client proteins to be destabilized and eventually degraded. HDAC6 is an attractive target for cancer treatment because acetylated Hsp90 has a reduced ability to perform its chaperoning function (Butler, K. V. et al. 2008; Kovacs, J. J. et al. 2005), with consequent activation of the intrinsic pathway of apoptosis.

In general, for diseases caused by aberrant gene transcription, the most effective treatment would involve targeting only the genes relevant to the disease (Butler, K. V. et al. 2008). In the context of HDAC inhibitor treatment, this would involve inhibiting only those HDAC isoforms relevant to the disease state, thereby minimizing changes not related to the disease, and possibly reducing side effects and toxicity. While SAHA combines efficacy with minimum toxicity, its inhibitory activity is not selective among the known human HDACs.

Marks & Breslow (Marks, P. et al. 2007; Marks, P. et al. 2010) describes the development of HDAC inhibitor vorinostat as an anti-cancer drug. HDAC inhibitors have also been identified as a correction for cholesterol and sphingolipid transport defects in human Niemann-Pick type C disease (Munkacsi, A. B. et al. 2011).

In view of the importance of inhibiting only those HDAC isoforms relevant to a disease state, minimizing acetylation of proteins not related to the disease, and reducing side effects and toxicity, new HDAC inhibitors that are selective for specific HDACs are needed.

SUMMARY OF THE INVENTION

The present invention provides a compound having the structure:

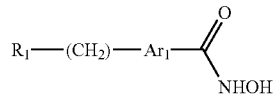

wherein
R$_1$ is halogen, —NR$_5$R$_6$, —NR$_5$—C(=O)—R$_6$, —NH—C(=O)—OR$_7$, —OR$_7$, —NO$_2$, —CN, —SR$_7$, —SO$_2$R$_7$, —CO$_2$R$_7$, CF$_3$, —SOR$_7$, —POR$_7$, —C(=S)R$_7$, —C(=O)—NR$_5$R$_6$, —CH$_2$—C(=O)—NR$_5$R$_6$, —C(=NR$_5$)R$_6$, —P(=O)(OR$_5$)(OR$_6$), —P(OR$_5$)(OR$_6$), —C(=S)R$_7$, C$_{1-5}$ alkyl, C$_{2-5}$ alkenyl, C$_{2-5}$ alkynyl, aryl, heteroaryl, or heterocyclyl,
wherein R$_5$, R$_6$, and R$_7$ and are each, independently, H, C$_{1-5}$ alkyl, C$_{2-5}$ alkenyl, C$_{2-5}$ alkynyl, heteroalkyl, hydroxyalkyl, cycloalkyl, heterocycloalkyl, aryl, heteroaryl, C$_{1-5}$ alkyl-aryl, or C$_{1-5}$ alkyl-NH-aryl;
Ar$_1$ is phenyl or thiophene;
wherein when Ar$_1$ is phenyl, then R$_1$ is other than —C(=O)—NR$_5$R$_6$, where one of R$_5$ or R$_6$ is phenyl or quinoline and the other of R$_5$ or R$_6$ is —CH$_2$CH$_2$OH, or where one of R$_5$ or R$_6$ is quinoline and the other of R$_5$ or R$_6$ is H; and wherein when $Ar_1$ is phenyl, then $R_1$ is other than —$NR_5$—C(=O)—$R_6$, where $R_5$ is H and $R_6$ is quinoline, or a pharmaceutically acceptable salt thereof.

DETAILED DESCRIPTION OF THE INVENTION

Figure 1:
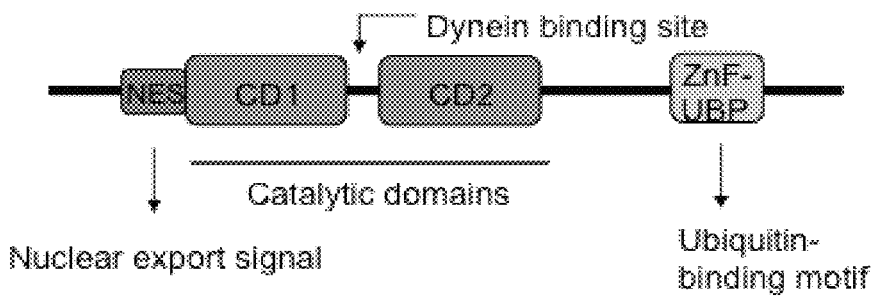
FIG. 1. Schematic representation of HDAC6.

The present invention provides a compound having the structure:

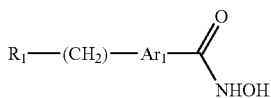

wherein
$R_1$ is halogen, —$NR_5R_6$, —$NR_5$—C(=O)—$R_6$, —NH—C(=O)—$OR_7$, —$OR_7$, —$NO_2$, —CN, —$SR_7$, —$SO_2R_7$, —$CO_2R_7$, $CF_3$, —$SOR_7$, —$POR_7$, —C(=S)$R_7$, —C(=O)—$NR_5R_6$, —$CH_2$—C(=O)—$NR_5R_6$, —C(=$NR_5$)$R_6$, —P(=O)($OR_5$)($OR_6$), —P($OR_5$)($OR_6$), —C(=S)$R_7$, $C_{1-5}$ alkyl, $C_{2-5}$ alkenyl, $C_{2-5}$ alkynyl, aryl, heteroaryl, or heterocyclyl,
wherein $R_5$, $R_6$, and $R_7$ and are each, independently, H, $C_{1-5}$ alkyl, $C_{2-5}$ alkenyl, $C_{2-5}$ alkynyl, heteroalkyl, hydroxyalkyl, cycloalkyl, heterocycloalkyl, aryl, heteroaryl, $C_{1-5}$ alkyl-aryl, or $C_{1-5}$ alkyl-NH-aryl;
$Ar_1$ is phenyl or thiophene;
wherein when $Ar_1$ is phenyl, then $R_1$ is other than —C(=O)—$NR_5R_6$, where one of $R_5$ or $R_6$ is phenyl or quinoline and the other of $R_5$ or $R_6$ is —$CH_2CH_2OH$, or where one of $R_5$ or $R_6$ is quinoline and the other of $R_5$ or $R_6$ is H; and
wherein when $Ar_1$ is phenyl, then $R_1$ is other than —$NR_5$—C(=O)—$R_6$, where $R_5$ is H and $R_6$ is quinoline, or a pharmaceutically acceptable salt thereof.

In some embodiments, the compound wherein $Ar_1$ is

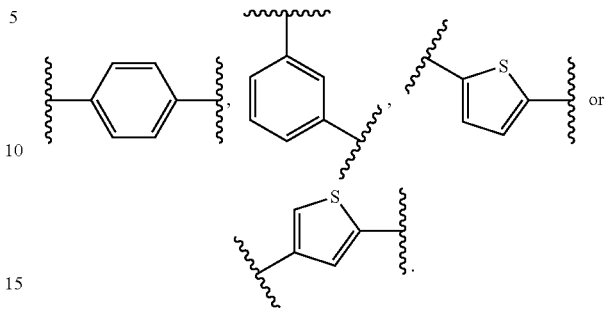

In some embodiments, the compound wherein
$R_1$ is —C(=O)—$NR_5R_6$, —$NR_5$—C(=O)—$R_6$, or —$CO_2R_7$,
wherein $R_5$, $R_6$, and $R_7$ and are each, independently, H, $C_{1-5}$ alkyl, $C_{2-5}$ alkenyl, $C_{2-5}$ alkynyl, heteroalkyl, hydroxyalkyl, cycloalkyl, heterocycloalkyl, aryl, heteroaryl, $C_{1-5}$ alkyl-aryl, or $C_{1-5}$ alkyl-NH-aryl.

In some embodiments, the compound wherein
$R_1$ is —C(=O)—$NR_5R_6$, —$NR_5$—C(=O)—$R_6$, or —$CO_2R_7$,
wherein $R_5$, $R_6$, and $R_7$ and are each, independently, H, $C_{1-5}$ alkyl, hydroxyalkyl, aryl, heteroaryl, $C_{1-5}$ alkyl-aryl, or $C_{1-5}$ alkyl-NH-aryl.

In some embodiments, the compound wherein
$R_1$ is —C(=O)—$NR_5R_6$, —$NR_5$—C(=O)—$R_6$, or —$CO_2R_7$,
wherein
$R_5$ is $C_{1-5}$ alkyl, hydroxyalkyl, aryl or heteroaryl;
$R_6$ is $C_{1-5}$ alkyl, hydroxyalkyl, aryl or heteroaryl; and
$R_7$ is $C_{1-5}$ alkyl, hydroxyalkyl, aryl, heteroaryl, or $C_{1-5}$ alkyl-NH-aryl.

In some embodiments, the compound wherein
$R_1$ is —C(=O)—$NR_5R_6$, —$NR_5$—C(=O)—$R_6$, or —$CO_2R_7$,
wherein $R_5$, $R_6$, and $R_7$ and are each, independently, phenyl, —$CH_2CH_2OH$, —$CH_2$-phenyl, or —$CH_2CH_2N(H)$-phenyl.

In some embodiments, the compound wherein
$R_1$ is —C(=O)—$NR_5R_6$, —$NR_5$—C(=O)—$R_6$, or —$CO_2R_7$,
wherein $R_5$, $R_6$, and $R_7$ and are each, independently,

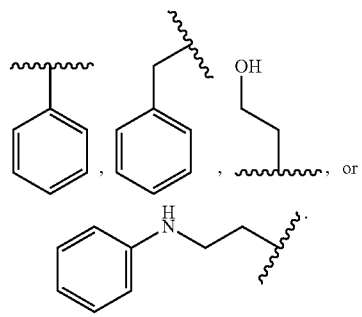

In some embodiments, the compound wherein
R$_1$ is —C(=O)—NR$_5$R$_6$,
wherein R$_5$ is

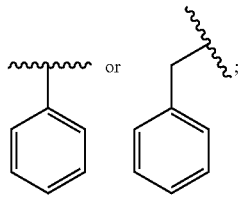

and R$_6$ is

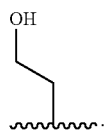

In some embodiments, the compound wherein
R$_1$ is —NR$_5$—C(=O)
wherein R$_5$ is

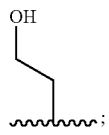

and R$_6$ is

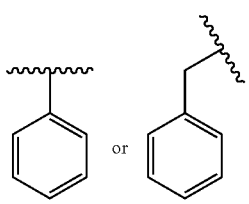

In some embodiments, the compound wherein
R$_1$ is —CO$_2$R$_7$,
wherein R$_7$

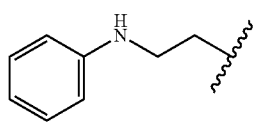

The present invention provides a compound having the structure:

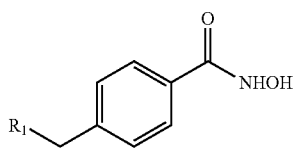

wherein
R$_1$ is halogen, —NR$_5$R$_6$, —NR$_5$—C(=O)—R$_6$, —OR$_7$, —NO$_2$, —CN, —SO$_2$R$_7$, —CO$_2$R$_7$, CF$_3$, —SOR$_7$, —POR$_7$, —C(=S)R$_7$, —C(=O)—NR$_5$R$_6$, —CH$_2$—C(=O)—NR$_5$R$_6$, —C(=NR$_5$)R$_6$, —P(=O)(OR$_5$)(OR$_6$), —P(OR$_5$)(OR$_6$), —C(=S)R$_7$, C$_{1-5}$ alkyl, C$_{2-5}$ alkenyl, C$_{2-5}$ alkynyl, aryl, heteroaryl, or heterocyclyl,
wherein R$_5$, R$_6$, and R$_7$ and are each, independently, H, C$_{1-5}$ alkyl, C$_{2-5}$ alkenyl, C$_{2-5}$ alkynyl, heteroalkyl, hydroxyalkyl, cycloalkyl, heterocycloalkyl, aryl, heteroaryl, C$_{1-5}$ alkyl-aryl, or C$_{1-5}$ alkyl-NH-aryl;
wherein R$_1$ is other than —C(=O)—NR$_5$R$_6$, where one of R$_5$ or R$_6$ is phenyl or quinoline and the other of R$_5$ or R$_6$ is —CH$_2$CH$_2$OH, or where one of R$_5$ or R$_6$ is quinoline and the other of R$_5$ or R$_6$ is H; and
wherein R$_1$ is other than —NR$_5$—C(=O)—R$_6$, where R$_5$ is H and R$_6$ is quinoline,
or a pharmaceutically acceptable salt thereof.

In some embodiments, the compound wherein
R$_1$ is —C(=O)—NR$_5$R$_6$, —NR$_5$—C(=O)—R$_6$, or —CO$_2$R$_7$,
wherein R$_5$, R$_6$ and R$_7$ and are each, independently, H, alkyl, C$_{2-5}$ alkenyl, C$_{2-5}$ alkynyl, heteroalkyl, hydroxyalkyl, cycloalkyl, heterocycloalkyl, aryl, heteroaryl, C$_{1-5}$ alkyl-aryl, or C$_{1-5}$ alkyl-NH-aryl.

In some embodiments, the compound wherein
R$_1$ is —C(=O)—NR$_5$R$_6$, —NR$_5$—C(=O)—R$_6$, or —CO$_3$R$_7$,
wherein R$_5$, R$_6$, and R$_7$ and are each, independently, H, C$_{1-5}$ alkyl, hydroxyalkyl, aryl, heteroaryl, C$_{1-5}$ alkyl-aryl, or C$_{1-5}$ alkyl-NH-aryl.

In some embodiments, the compound wherein
R$_1$ is —C(=O)—NR$_5$R$_6$, (=O)—R$_6$, or —CO$_2$R$_7$
wherein
R$_5$ is C$_{1-5}$ alkyl, hydroxyalkyl, aryl or heteroaryl;
R$_6$ is C$_{1-5}$ alkyl, hydroxyalkyl, aryl or heteroaryl; and
R$_7$ is C$_{1-5}$ alkyl, hydroxyalkyl, aryl, heteroaryl, or C$_{1-5}$ alkyl-NH-aryl.

In some embodiments, the compound wherein
R$_1$ is —C(=O)—NR$_5$R$_6$, —NR$_5$—C(=O)—R$_6$, or —CO$_2$R$_7$,
wherein R$_5$, R$_6$, and R$_7$ and are each, independently, phenyl, —CH$_2$CH$_2$OH, —CH$_2$-phenyl, or —CH$_2$CH$_2$N(H)-phenyl.

In some embodiments, the compound wherein
R$_1$ is —C(=O)—NR$_5$R$_6$, —NR$_5$—C(=O)—R$_6$, or —CO$_2$R$_7$,
wherein R$_5$, R$_6$, and R$_7$ and are each, independently,

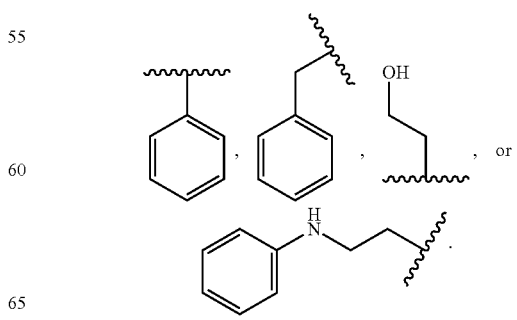

In some embodiments, the compound wherein
R₁ is —C(=O)—NR₅R₆,
  wherein R₅ is

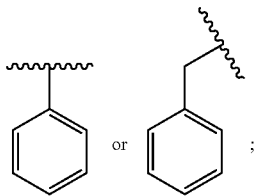 [SMILES: *c1ccccc1 ; *Cc1ccccc1]

and R₆ is

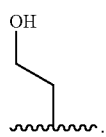

In some embodiments, the compound wherein
R₁ is —NR₅—C(=O)—R₆,
  wherein R₅ is

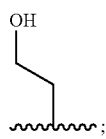

and R₆ is

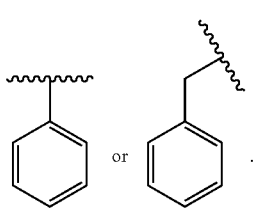 [SMILES: *c1ccccc1 ; *Cc1ccccc1]

In some embodiments, the compound wherein
R₁ is —CO₂R₇,
  wherein R₇

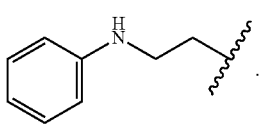 [SMILES: *CCNc1ccccc1]

The present invention provides a compound having the structure:

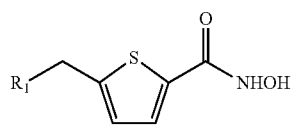

wherein
R₁ is halogen, —NR₅R₆, —NR₅—C(=O)—R₆, —NH—C(=O)—OR₇, —OR₇, —NO₂, —CN, —SR₇, —SO₂R₇, —CO₂R₇, CF₃, —SOR₇, —POR₇, —C(=S)R₇, —C(=O)—NR₅R₆, —CH₂—C(=O)—NR₅R₆, —C(=NR₅)R₆, —P(=O)(OR₅)(OR₆), —P(OR₅)(OR₆), —C(=S)R₇, C₁₋₅ alkyl, C₂₋₅ alkenyl, C₂₋₅ alkynyl, aryl, heteroaryl, or heterocyclyl,
  wherein R₅, R₆, and R₇ and are each, independently, H, C₁₋₅ alkyl, C₂₋₅ alkenyl, C₂₋₅ alkynyl, heteroalkyl, hydroxyalkyl, cycloalkyl, heterocycloalkyl, aryl, heteroaryl, C₁₋₅ alkyl-aryl, or C₁₋₅ alkyl-NH-aryl,
or a pharmaceutically acceptable salt thereof.

In some embodiments, the compound wherein
R₁ is —C(=O)—NR₅R₆, —NR₅—C(=O)—R₆, or —CO₂R₇,
  wherein R₅, R₆, and R₇ and are each, independently, H, C₁₋₅ alkyl, C₂₋₅ alkenyl, C₂₋₅ alkynyl, heteroalkyl, hydroxyalkyl, cycloalkyl, heterocycloalkyl, aryl, heteroaryl, C₁₋₅ alkyl-aryl, or C₁₋₅ alkyl-NH-aryl.

In some embodiments, the compound wherein
R₁ is —C(=O)—NR₅R₆, —NR₅—C(=O)—R₆, or —CO₂R₇,
  wherein R₅, R₆, and R₇ and are each, independently, H, C₁₋₅ alkyl, hydroxyalkyl, aryl, heteroaryl, C₁₋₅ alkyl-aryl, or C₁₋₅ alkyl-NH-aryl.

In some embodiments, the compound wherein
R₁ is —C(=O)—NR₅R₆, —NR₅—C(=O)—R₆, or —CO₂R₇
wherein
R₅ is C₁₋₅ alkyl, hydroxyalkyl, aryl or heteroaryl;
R₆ is C₁₋₅ alkyl, hydroxyalkyl, aryl or heteroaryl; and
R₇ is C₁₋₅ alkyl, hydroxyalkyl, aryl, heteroaryl, or C₁₋₅ alkyl-NH-aryl.

In some embodiments, the compound wherein
R₁ is —C(=O)—NR₅R₆, —NR₅—C(=O)—R₆, or —CO₂R₇,
  wherein R₅, R₆, and R₇ and are each, independently, phenyl, —CH₂CH₂OH, —CH₂-phenyl, or —CH₂CH₂N(H)-phenyl.

In some embodiments, the compound wherein
R₁ is —C(=O)—NR₅R₆, —NR₅—C(=O)—R₆, or —CO₂R₇,
  wherein R₅, R₆, and R₇ and are each, independently,

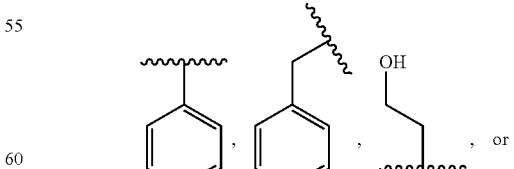

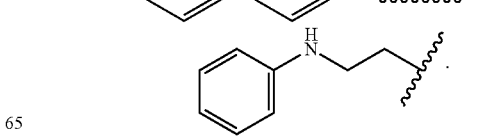

In some embodiments, the compound wherein
R$_1$ is —C(=O)—NR$_5$R$_6$,
wherein R$_5$ is

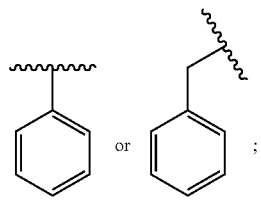 [SMILES: *c1ccccc1 ; *Cc1ccccc1]

and R$_6$ is

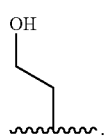

In some embodiments, the compound wherein
R$_1$ is —NR$_5$—C(=O)—R$_6$,
wherein R$_5$ is

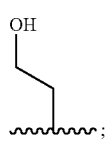

and R$_6$ is

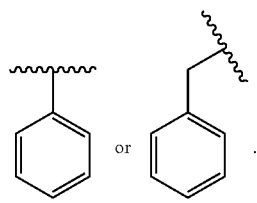 [SMILES: *c1ccccc1 ; *Cc1ccccc1]

In some embodiments, the compound wherein
R$_1$ is —CO$_2$R$_7$,
wherein R$_7$

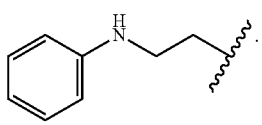 [SMILES: *CCNc1ccccc1]

In some embodiments, the compound wherein
R$_1$ is —C(=O)—NR$_5$R$_6$, —NR$_5$—C(=O)—R$_6$, or —CO$_2$R$_7$,
wherein
R$_5$ is C$_{1-5}$ alkyl, hydroxyalkyl, aryl or heteroaryl;
R$_6$ is C$_{1-5}$ alkyl, hydroxyalkyl, aryl or heteroaryl; and
R$_7$ is C$_{1-5}$ alkyl, hydroxyalkyl, aryl, heteroaryl, or C$_{1-5}$ alkyl-NH-aryl; and
Ar$_1$ is phenyl or thiophene,
or a pharmaceutically acceptable salt thereof.

In some embodiments, the compound wherein
R$_1$ is —C(=O)—NR$_5$R$_6$, —NR$_5$—C(=O)—R$_6$, or —CO$_2$R$_7$,
wherein
R$_5$ is C$_{1-5}$ alkyl, hydroxyalkyl, aryl or heteroaryl;
R$_6$ is C$_{1-5}$ alkyl, hydroxyalkyl, aryl or heteroaryl; and
R$_7$ is C$_{1-5}$ alkyl, hydroxyalkyl, aryl, heteroaryl, or C$_{1-5}$ alkyl-NH-aryl; and
Ar$_1$ is

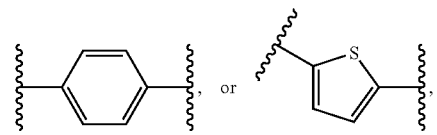 [SMILES: *c1ccc(*)cc1 ; *c1ccc(*)s1]

or a pharmaceutically acceptable salt thereof.

In some embodiments, the compound having the structure:

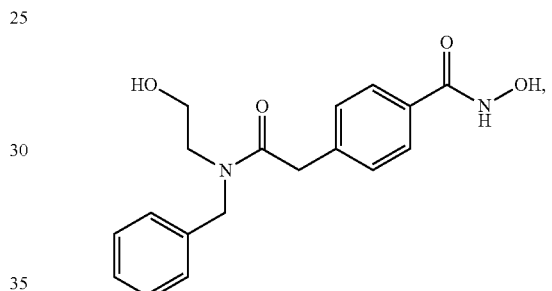

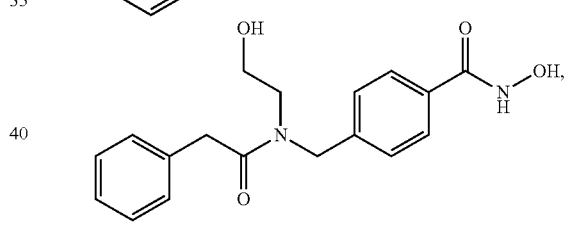

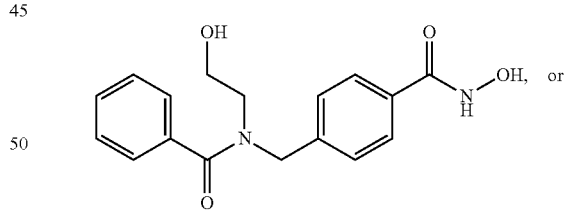

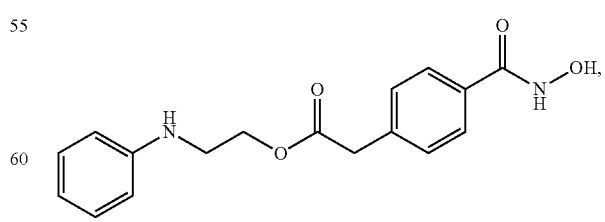

or a pharmaceutically acceptable salt thereof.

In some embodiments, the compound having the structure:

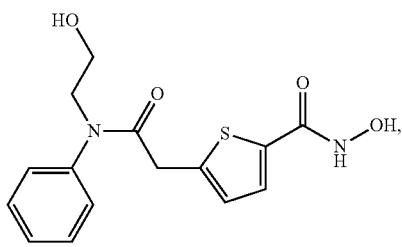 [SMILES: O=C(NO)c1ccc(CC(=O)N(CCO)c2ccccc2)s1]

or a pharmaceutically acceptable salt thereof.

The present invention provides pharmaceutical composition comprising the compound of the present invention and a pharmaceutically acceptable carrier.

The present invention provides a method of inhibiting the activity of a histone deactylase in a cell comprising contacting the histone deacetylase with the compound of the present invention so as to inhibit the activity of the histone deacetylase. In some embodiments, the histone deacetylase is HDAC6.

The present invention provides a method of inhibiting the activity of a histone deacetylase 6 (HDAC6) in a cell comprising contacting the histone deacetylase 6 with the compound of the present invention so as to inhibit the activity of the histone deacetylase 6 in the cell.

The present invention provides a method of increasing accumulation of acetylated alpha-tubulin in a cell comprising contacting the cell with the compound of the present invention so as to increase the accumulation of acetylated alpha-tubulin in the cell.

The present invention provides a method of treating a neurodegenerative disease in a subject comprising administering an effective amount of the compound of the present invention to the subject so as to treat the neurodegenerative disease in the subject. In some embodiments, the method wherein the neurodegenerative disease is Parkinson's disease, Alzheimer's disease, Huntington's disease or Niemann-Pick type C disease.

The present invention provides a method of treating a disease associated with defective lipid transport in a subject comprising administering an effective amount of the compound of the present invention to the subject so as to treat the disease in the subject.

In some embodiments, the method wherein the disease associated with defective lipid transport is Stargardt disease, macular degeneration, Harlequin ichthyosis or Tangier disease.

The present invention provides a method of treating cancer in a subject comprising administering an effective amount of the compound of the present invention to the subject so as to treat the cancer in the subject.

The present invention provides a method of treating HIV infection in a subject comprising administering an effective amount of the compound of the present invention to the subject so as to treat the HIV infection in the subject.

The present invention provides a method of treating latent HIV infection in a subject comprising administering an effective amount of the compound of the present invention to the subject so as to treat the latent HIV infection in the subject.

The present invention provides a method of enhancing the anti-cancer activity of an anti-cancer agent in a subject afflicted with a cancer, comprising administering to the subject the compound of the present invention in an amount effective to enhance the anti-cancer activity of the anti-cancer agent.

The present invention provides a method of treating a subject afflicted with cancer comprising periodically administering to the subject a) an amount of the compound of the present invention or a pharmaceutically acceptable salt thereof, and b) an anti-cancer agent, wherein the amounts when taken together are more effective to treat the subject than when each agent at the same amount is administered alone.

In some embodiments, the method wherein the anti-cancer agent is SAHA, etoposide or paclitaxel.

In some embodiments, the method wherein the anti-cancer agent is selected from x-radiation, ionizing radiation, a DNA damaging agent, a DNA intercalating agent, a microtubule stabilizing agent, a microtubule destabilizing agent, a spindle toxin, abarelix, aldesleukin, alemtuzumab, alitertinoin, allopurinol, altretamine, amifostin, anakinra, anastrozole, arsenic trioxide, asparaginase, azacitidine, bevacizumab, bexarotene, bleomycin, bortezomib, busulfan, calusterone, capecitabine, carboplatin, carmustine, celecoxib, cetuximab, chlorambucil, cisplatin, cladribine, clofarabine, cyclophosphamide, cytarabine, dacarbazine, dactinomycin, actinomycin D, dalteparin sodium, darbepoetin alfa, dasatinib, daunorubicin, daunomycin, decitabine, denileukin, dexrazoxane, docetaxel, doxorubicin, dromostanolone propionate, exulizumab, epirubicin, epoetin alfa, erlotinib, estramustine, etoposide phosphate, etoposide, VP-16, exemestane, fentanyl citrate, filgrastim, floxuridine, fludarabine, fluorouracil, fulvestrant, gefitinib, gemcitabine, gosereline acetate, histrelin acetate, hydroxyurea, ibritumomab tiuxetan, idarubicin, Ifosfamide, imatinib mesylate, interferon alfa 2a, interferon alfa 2b, irinotecan, lapatinib ditosylate, lenalidomide, letrozole, leucovrin, leuprolide acetate, levamisole, lomustine, meclorethamine, megestrol acetate, melphalan, mercaptopurine, mesna, methotrexate, methoxsalen, mitomycin C, mitotane, mitoxantrone, nandrolone phenpropionate, nelarabine, nofetumomab, oprelvekin, oxaliplatin, paclitaxel, palifermin, pamidronate, panitumumab, pegademase, pegaspargase, pegfilgrastim, peginterferon alfa 2b, pemetrexed disodium, pentostatin, pipobroman, plicamycin, mithramycin, porfimer sodium, procarbazine, quinacrine, rasburicase, rituximab, SAHA, sargrmostim, sorafenib, streptozocin, sunitinib, sunitinib maleate, talc, tamoxifen, temozolomide, teniposide, VM-26, testolactone, thalidomide, thioguanine, G-TG, thiotepa, topotecan, toremifene, tositumomab, trastuzumab, tretinoin ATRA, uracil mustard, valrunicin, vinblastine, vincristine, vinorelbine, vorinostat, zoledronate, zoledronic acid, abraxane or brentuximab vedotin.

In some embodiments, a pharmaceutical composition comprising the compound of the present invention or a pharmaceutically acceptable salt thereof and an anti-cancer agent, and at least one pharmaceutically acceptable carrier.

In some embodiments, the use of the compound of the present invention or a pharmaceutically acceptable salt thereof and an anti-cancer agent in the preparation of a combination for treating a subject afflicted with cancer wherein the amount of the compound and the amount of the anti-cancer agent are administered simultaneously or contemporaneously.

In some embodiments, a pharmaceutical composition comprising an amount of the compound of the present invention or a pharmaceutically acceptable salt thereof for use in treating a subject afflicted with cancer as an add-on therapy or in combination with, or simultaneously, contemporaneously or concomitantly with an anti-cancer agent.

In some embodiments, the compound of the present invention or a pharmaceutically acceptable salt thereof for use as an add-on therapy or in combination with an anti-cancer agent in treating a subject afflicted with cancer.

In some embodiments, the compound of the present invention or a pharmaceutically acceptable salt thereof and an anti-cancer agent for the treatment of a subject afflicted with cancer wherein the compound and the anti-cancer agent are administered simultaneously, separately or sequentially.

In some embodiments, the subject is a human.

In some embodiments, a product containing an amount of the compound of the present invention or a pharmaceutically acceptable salt thereof and an amount of an anti-cancer agent for simultaneous, separate or sequential use in treating a subject afflicted cancer.

In some embodiments, the compound of the present invention or a pharmaceutically acceptable salt thereof in combination with an anti-cancer agent for use in treating cancer.

In some embodiments, a pharmaceutical composition comprising the compound of the present invention and a pharmaceutically acceptable carrier.

In some embodiments, a method of inhibiting the activity of a histone deactylase in a cell comprising contacting the histone deacetylase with the compound or composition of the present invention so as to inhibit the activity of the histone deacetylase.

In some embodiments, a method of inhibiting the activity of a histone deactylase, wherein the histone deacetylase is HDAC6.

In some embodiments, a method of inhibiting the activity of a histone deacetylase 6 (HDAC6) in a cell comprising contacting the histone deacetylase 6 with the compound or composition of the present invention so as to inhibit the activity of the histone deacetylase 6 in the cell.

In some embodiments, a method of increasing accumulation of acetylated alpha-tubulin in a cell comprising contacting the cell with any one of the compound or composition of the present invention so as to increase the accumulation of acetylated alpha-tubulin in the cell.

In some embodiments, a method of treating a neurodegenerative disease in a subject comprising administering an effective amount of the compound or composition of the present invention to the subject so as to treat the neurodegenerative disease in the subject.

In some embodiments, a method of treating a neurodegenerative disease wherein the neurodegenerative disease is Parkinson's disease, Alzheimer's disease, Huntington's disease or Niemann-Pick type C disease.

In some embodiments, a method of treating a disease associated with defective lipid transport in a subject comprising administering an effective amount of the compound or composition of the present invention to the subject so as to treat the disease in the subject.

In some embodiments, a method of treating a disease associated with defective lipid transport wherein the disease associated with defective lipid transport is Stargardt disease, macular degeneration, Harlequin ichthyosis or Tangier disease.

A method of inhibiting the activity of a histone deactylase in a cell comprising contacting the histone deacetylase with any one, or more, of the instant compounds so as to inhibit the activity of the histone deacetylase. In an embodiment the histone deacetylase is HDAC6.

A method of inhibiting the activity of a histone deacetylase 6 (HDAC6) in a cell comprising contacting the histone deacetylase 6 with any one, or more, of the instant compounds so as to inhibit the activity of the histone deacetylase 6 in the cell.

A method of increasing accumulation of acetylated alpha tubulin in a cell comprising contacting the cell with any one, or more, of the instant compounds so as to increase the accumulation of acetylated alpha-tubulin in the cell.

In some embodiments, a method for reducing one or more symptoms of disease in a subject, comprising administering an effective amount of the compound of the present invention or the composition of the present invention to the subject so as to treat the disease in the subject.

In some embodiments, a method of treating cancer in a subject comprising administering an effective amount of the compound of the present invention to the subject so as to treat the cancer in the subject.

In some embodiments, a method for inhibiting the growth of a tumor comprising contacting the tumor with the compound of the present invention or the composition of the present invention. In some embodiments, a method for reducing the size of a tumor comprising contacting the tumor with the compound of the present invention or the composition of the present invention In some embodiments, the invention provides a method of reducing one or more symptoms of any disease that involves carcinomas including but not limited to lung cancer, breast cancer, prostate cancer, cervical cancer, pancreatic cancer, colon cancer, ovarian cancer; stomach cancer, esophagus cancer, mouth cancer, tongue cancer, gum cancer, skin cancer (e.g., melanoma, basal cell carcinoma, Kaposi's sarcoma, etc.), muscle cancer, heart cancer, liver cancer, bronchial cancer, cartilage cancer, bone cancer, testis cancer, kidney cancer, endometrium cancer, uterus cancer, bladder cancer, bone marrow cancer, lymphoma cancer, spleen cancer, thymus cancer, thyroid cancer, brain cancer, neuron cancer, mesothelioma, gall bladder cancer, ocular cancer (e.g., cancer of the cornea, cancer of uvea, cancer of the choroids, cancer of the macula, vitreous humor cancer, etc.), joint cancer (such as synovium cancer), glioblastoma, lymphoma, and leukemia. Malignant neoplasms are further exemplified by sarcomas (such as osteosarcoma and Kaposi's sarcoma).

In some embodiments, a method of treating HIV infection in a subject comprising administering an effective amount of the compound of the present invention to the subject so as to treat the HIV infection in the subject.

In some embodiments, a method of treating latent HIV infection in a subject comprising administering an effective amount of the compound of the present invention to the subject so as to treat the latent HIV infection in the subject.

In some embodiments, a method wherein the subject is infected with HIV. In some embodiments, the invention provides a method of reducing one or more symptoms of HIV infection. In some embodiments, a method of inhibiting HIV replication by contacting an HIV-infected cell with the compound of the present invention. In some embodiments, the HIV-infected cells are HIV reservoir cells.

This invention also provides isotopic variants of the compounds disclosed herein, including wherein the isotopic atom is $^2H$ and/or wherein the isotopic atom $^{13}C$. Accordingly, in the compounds provided herein hydrogen can be enriched in the deuterium isotope. It is to be understood that the invention encompasses all such isotopic forms which inhibit HDAC, including those which inhibit HDAC6 selectively over HDAC1.

A method of treating a neurodegenerative disease in a subject comprising administering an effective amount of any one, or more, of the instant compounds to the subject so as to treat the neurodegenerative disease in the subject.

In an embodiment, the neurodegenerative disease is Parkinson's disease, Alzheimer's disease, Huntington's disease or Niemann-Pick type C disease.

A method of treating a disease associated with defective lipid transport in a subject comprising administering an effective amount of any one, or more, of the instant compounds to the subject so as to treat the disease in the subject.

In an embodiment, the disease associated with defective lipid transport is Stargardt disease, macular degeneration, Harlequin ichthyosis or Tangier disease.

In some embodiments of any one the above methods, uses, pharmaceutical compositions, compounds or products, the compound has the structure of compound 8, compound 11, compound 23, compound 32, or compound 36.

It is understood that the structures described in the embodiments of the methods can be the same as the structures of the compounds described hereinabove.

It is understood that where a numerical range is recited herein, the present invention contemplates each integer between, and including, the upper and lower limits, unless otherwise stated.

As used herein, the term "activity" refers to the activation, production, expression, synthesis, intercellular effect, and/or pathological or aberrant effect of the referenced molecule, either inside and/or outside of a cell. Such molecules include, but are not limited to, cytokines, enzymes, growth factors, pro-growth factors, active growth factors, and pro-enzymes. Molecules such as cytokines, enzymes, growth factors, pro-growth factors, active growth factors, and pro-enzymes may be produced, expressed, or synthesized within a cell where they may exert an effect. Such molecules may also be transported outside of the cell to the extracellular matrix where they may induce an effect on the extracellular matrix or on a neighboring cell. It is understood that activation of inactive cytokines, enzymes and pro-enzymes may occur inside and/or outside of a cell and that both inactive and active forms may be present at any point inside and/or outside of a cell. It is also understood that cells may possess basal levels of such molecules for normal function and that abnormally high or low levels of such active molecules may lead to pathological or aberrant effects that may be corrected by pharmacological intervention.

As used herein, the term "histone deacetylase" or "HDAC" refers to any member of the classes of enzymes capable of cleaving an acetyl group (—C(=O)CH$_3$) from proteins, which include, but are not limited to, histones and microtubules. A histone deacetylase may be zinc-dependent. Examples of HDACs include, but are not limited to, HDAC1, HDAC2, HDAC3, HDAC4, HDAC5, HDAC6, HDAC7, HDAC8, HDAC9, HDAC10, and HDAC11.

Except where otherwise specified, the structure of a compound of this invention includes an asymmetric carbon atom, it is understood that the compound occurs as a racemate, racemic mixture, and isolated single enantiomer. All such isomeric forms of these compounds are expressly included in this invention. Except where otherwise specified, each stereogenic carbon may be of the R or S configuration. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis, such as those described in "Enantiomers, Racemates and Resolutions" by J. Jacques, A. Collet and S. Wilen, Pub. John Wiley & Sons, NY, 1981. For example, the resolution may be carried out by preparative chromatography on a chiral column.

The subject invention is also intended to include all isotopes of atoms occurring on the compounds disclosed herein. Isotopes include those atoms having the same atomic number but different mass numbers. By way of general example and without limitation, isotopes of hydrogen include tritium and deuterium. Isotopes of carbon include C-13 and C-14.

It will be noted that any notation of a carbon in structures throughout this application, when used without further notation, are intended to represent all isotopes of carbon, such as $^{12}$C, $^{13}$C, or $^{14}$C. Furthermore, any compounds containing $^{13}$C or $^{14}$C may specifically have the structure of any of the compounds disclosed herein.

It will also be noted that any notation of a hydrogen in structures throughout this application, when used without further notation, are intended to represent all isotopes of hydrogen, such as $^1$H, $^2$H, or $^3$H. Furthermore, any compounds containing $^2$H or $^3$H may specifically have the structure of any of the compounds disclosed herein.

Isotopically-labeled compounds can generally be prepared by conventional techniques known to those skilled in the art using appropriate isotopically-labeled reagents in place of the non-labeled reagents employed.

In the compounds used in the method of the present invention, the substituents may be substituted or unsubstituted, unless specifically defined otherwise.

In the compounds used in the method of the present invention, alkyl, heteroalkyl, monocycle, bicycle, aryl, heteroaryl and heterocycle groups can be further substituted by replacing one or more hydrogen atoms with alternative non-hydrogen groups. These include, but are not limited to, halo, hydroxy, mercapto, amino, carboxy, cyano and carbamoyl.

It is understood that substituents and substitution patterns on the compounds used in the method of the present invention can be selected by one of ordinary skill in the art to provide compounds that are chemically stable and that can be readily synthesized by techniques known in the art from readily available starting materials. If a substituent is itself substituted with more than one group, it is understood that these multiple groups may be on the same carbon or on different carbons, so long as a stable structure results.

In choosing the compounds used in the method of the present invention, one of ordinary skill in the art will recognize that the various substituents, i.e. $R_1$, $R_2$, etc. are to be chosen in conformity with well-known principles of chemical structure connectivity.

As used herein, "alkyl" includes both branched and straight-chain saturated aliphatic hydrocarbon groups having the specified number of carbon atoms and may be unsubstituted or substituted. Thus, $C_1$-$C_n$ as in "$C_1$-$C_n$ alkyl" is defined to include groups having 1, 2, . . . , n–1 or n carbons in a linear or branched arrangement (e.g. $C_1$-$C_2$ alkyl, $C_1$-$C_3$ alkyl, $C_1$-$C_4$ alkyl, $C_1$-$C_5$ alkyl, or $C_1$-$C_6$ alkyl) For example, $C_1$-$C_6$, as in "$C_1$-$C_6$ alkyl" is defined to include groups having 1, 2, 3, 4, 5, or 6 carbons in a linear or branched arrangement, and specifically includes methyl, ethyl, n-propyl, isopropyl, n-butyl, t-butyl, pentyl, hexyl, and octyl.

As used herein, "alkenyl" refers to a non-aromatic hydrocarbon radical, straight or branched, containing at least 1 carbon to carbon double bond, and up to the maximum possible number of non-aromatic carbon-carbon double bonds may be present, and may be unsubstituted or substituted. For example, "C$_2$-C$_6$ alkenyl" means an alkenyl radical having 2, 3, 4, 5, or 6 carbon atoms, and up to 1, 2, 3, 4, or 5 carbon-carbon double bonds respectively. Alkenyl groups include ethenyl, propenyl, butenyl and cyclohexenyl.

The term "alkynyl" refers to a hydrocarbon radical straight or branched, containing at least 1 carbon to carbon triple bond, and up to the maximum possible number of non-aromatic carbon-carbon triple bonds may be present, and may be unsubstituted or substituted. Thus, "C$_2$-C$_6$ alkynyl" means an alkynyl radical having 2 or 3 carbon atoms and 1 carbon-carbon triple bond, or having 4 or 5 carbon atoms and up to 2 carbon-carbon triple bonds, or having 6 carbon atoms and up to 3 carbon-carbon triple bonds. Alkynyl groups include ethynyl, propynyl and butynyl.

"Alkylene", "alkenylene" and "alkynylene" shall mean, respectively, a divalent alkane, alkene and alkyne radical, respectively. It is understood that an alkylene, alkenylene, and alkynylene may be straight or branched. An alkylene, alkenylene, and alkynylene may be unsubstituted or substituted.

As used herein, "aryl" is intended to mean any stable monocyclic, bicyclic or polycyclic carbon ring of up to 10 atoms in each ring, wherein at least one ring is aromatic, and may be unsubstituted or substituted. Examples of such aryl elements include phenyl, p-toluenyl (4-methylphenyl), naphthyl, tetrahydro-naphthyl, indanyl, biphenyl, phenanthryl, anthryl or acenaphthyl. In cases where the aryl substituent is bicyclic and one ring is non-aromatic, it is understood that attachment is via the aromatic ring.

As used herein, the term "polycyclic" refers to unsaturated or partially unsaturated multiple fused ring structures, which may be unsubstituted or substituted.

The term "arylalkyl" refers to alkyl groups as described above wherein one or more bonds to hydrogen contained therein are replaced by a bond to an aryl group as described above. It is understood that an "arylalkyl" group is connected to a core molecule through a bond from the alkyl group and that the aryl group acts as a substituent on the alkyl group. Examples of arylalkyl moieties include, but are not limited to, benzyl (phenylmethyl), p-trifluoromethylbenzyl (4-trifluoromethylphenylmethyl), 1-phenylethyl, 2-phenylethyl, 3-phenylpropyl, 2-phenylpropyl and the like.

The term "heteroaryl", as used herein, represents a stable monocyclic, bicyclic or polycyclic ring of up to 10 atoms in each ring, wherein at least one ring is aromatic and contains from 1 to 4 heteroatoms selected from the group consisting of O, N and S. Bicyclic aromatic heteroaryl groups include phenyl, pyridine, pyrimidine or pyridizine rings that are (a) fused to a 6-membered aromatic (unsaturated) heterocyclic ring having one nitrogen atom; (b) fused to a 5- or 6-membered aromatic (unsaturated) heterocyclic ring having two nitrogen atoms; (c) fused to a 5-membered aromatic (unsaturated) heterocyclic ring having one nitrogen atom together with either one oxygen or one sulfur atom; or (d) fused to a 5-membered aromatic (unsaturated) heterocyclic ring having one heteroatom selected from O, N or S. Heteroaryl groups within the scope of this definition include but are not limited to benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrazolyl, tetrazolopyridyl, thiadiazolyl, triazolyl, thienyl, triazolyl, azetidinyl, aziridinyl, 1,4-dioxanyl, hexahydroazepinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, tetrahydrothienyl, acridinyl, carbazolyl, cinnolinyl, quinoxalinyl, pyrazolyl, indolyl, benzotriazolyl, benzothiazolyl, benzoxazolyl, isoxazolyl, isothiazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetra-hydroquinoline. In cases where the heteroaryl substituent is bicyclic and one ring is non-aromatic or contains no heteroatoms, it is understood that attachment is via the aromatic ring or via the heteroatom containing ring, respectively. If the heteroaryl contains nitrogen atoms, it is understood that the corresponding N-oxides thereof are also encompassed by this definition.

As used herein, "cycloalkyl" includes cyclic rings of alkanes of three to eight total carbon atoms, or any number within this range (i.e., cyclopropyl, cyclobutyl, cyclopentyl, cyclohexyl, cycloheptyl or cyclooctyl).

The term "heterocycle", "heterocyclyl" or "heterocyclic" refers to a mono- or poly-cyclic ring system which can be saturated or contains one or more degrees of unsaturation and contains one or more heteroatoms. Preferred heteroatoms include N, O, and/or S, including N-oxides, sulfur oxides, and dioxides. Preferably the ring is three to ten-membered and is either saturated or has one or more degrees of unsaturation. The heterocycle may be unsubstituted or substituted, with multiple degrees of substitution being allowed. Such rings may be optionally fused to one or more of another "heterocyclic" ring(s), heteroaryl ring(s), aryl ring(s), or cycloalkyl ring(s). Examples of heterocycles include, but are not limited to, tetrahydrofuran, pyran, 1,4-dioxane, 1,3-dioxane, piperidine, piperazine, pyrrolidine, morpholine, thiomorpholine, tetrahydrothiopyran, tetrahydrothiophene, 1,3-oxathiolane, and the like.

As used herein, "heterocycloalkyl" is intended to mean a 5- to 10-membered nonaromatic ring containing from 1 to 4 heteroatoms selected from the group consisting of O, N and S, and includes bicyclic groups. "Heterocycloalkyl" therefore includes, but is not limited to the following: imidazolyl, piperazinyl, piperidinyl, pyrrolidinyl, morpholinyl, thiomorpholinyl, tetrahydropyranyl, dihydropiperidinyl, tetrahydrothiophenyl and the like. If the heterocycle contains nitrogen, it is understood that the corresponding N-oxides thereof are also encompassed by this definition.

The alkyl, alkenyl, alkynyl, aryl, heteroaryl and heterocyclyl substituents may be substituted or unsubstituted, unless specifically defined otherwise.

In the compounds of the present invention, alkyl, alkenyl, alkynyl, aryl, heterocyclyl and heteroaryl groups can be further substituted by replacing one or more hydrogen atoms with alternative non-hydrogen groups. These include, but are not limited to, halo, hydroxy, mercapto, amino, carboxy, cyano and carbamoyl.

As used herein, the term "halogen" refers to F, Cl, Br, and I.

As used herein, "heteroalkyl" includes both branched and straight-chain saturated aliphatic hydrocarbon groups having the specified number of carbon atoms and at least 1 heteroatom within the chain or branch.

As used herein, "hydroxyalkyl" includes alkyl groups as described above wherein one or more bonds to hydrogen contained therein are replaced by a bond to an —OH group. In some embodiments, $C_1$-$C_{12}$ hydroxyalkyl or $C_1$-$C_6$ hydroxyalkyl. $C_1$-$C_n$ as in "$C_1$-$C_n$ alkyl" is defined to include groups having 1, 2, . . . , n–1 or n carbons in a linear or branched arrangement (e.g. $C_1$-$C_2$ hydroxyalkyl, $C_1$-$C_3$ hydroxyalkyl, $C_1$-$C_4$ hydroxyalkyl, $C_1$-$C_5$ hydroxyalkyl, or $C_1$-$C_6$ hydroxyalkyl) For example, $C_1$-$C_6$, as in "$C_1$-$C_6$ hydroxyalkyl" is defined to include groups having 1, 2, 3, 4, 5, or 6 carbons in a linear or branched alkyl arrangement wherein a hydrogen contained therein is replaced by a bond to an —OH group.

As used herein, "monocycle" includes any stable polyatomic carbon ring of up to 10 atoms and may be unsubstituted or substituted. Examples of such non-aromatic monocycle elements include but are not limited to: cyclobutyl, cyclopentyl, cyclohexyl, and cycloheptyl. Examples of such aromatic monocycle elements include but are not limited to: phenyl.

As used herein, "bicycle" includes any stable polyatomic carbon ring of up to 10 atoms that is fused to a polyatomic carbon ring of up to atoms with each ring being independently unsubstituted or substituted. Examples of such non-aromatic bicycle elements include but are not limited to: decahydronaphthalene. Examples of such aromatic bicycle elements include but are not limited to: naphthalene.

The term "alkylaryl" refers to alkyl groups as described above wherein one or more bonds to hydrogen contained therein are replaced by a bond to an aryl group as described above. It is understood that an "alkylaryl" group is connected to a core molecule through a bond from the alkyl group and that the aryl group acts as a substituent on the alkyl group. Examples of arylalkyl moieties include, but are not limited to, benzyl (phenylmethyl), p-trifluoromethylbenzyl (4-trifluoromethylphenylmethyl), 1-phenylethyl, 2-phenylethyl, 3-phenylpropyl, 2-phenylpropyl and the like.

The term "ester" is intended to a mean an organic compound containing the R—O—CO—R' group.

The term "amide" is intended to a mean an organic compound containing the R—CO—NH—R' or R—CO—N—R'R" group.

The term "phenyl" is intended to mean an aromatic six membered ring containing six carbons.

The term "thiophene" is intended to mean a heteroaryl having a five-membered ring containing four carbon atoms and one sulfur atom.

The term "quinoline" is intended to mean a fully aromatic heteroaryl having a six-membered ring fused to a six-membered ring containing nine carbon atoms and one nitrogen atom.

The term "substitution", "substituted" and "substituent" refers to a functional group as described above in which one or more bonds to a hydrogen atom contained therein are replaced by a bond to non-hydrogen or non-carbon atoms, provided that normal valencies are maintained and that the substitution results in a stable compound. Substituted groups also include groups in which one or more bonds to a carbon(s) or hydrogen(s) atom are replaced by one or more bonds, including double or triple bonds, to a heteroatom. Examples of substituent groups include the functional groups described above, and halogens (i.e., F, Cl, Br, and I); alkyl groups, such as methyl, ethyl, n-propyl, isopropyl, n-butyl, tert-butyl, and trifluoromethyl; hydroxyl; alkoxy groups, such as methoxy, ethoxy, n-propoxy, and iso-propoxy; aryloxy groups, such as phenoxy; arylalkyloxy, such as benzyloxy (phenylmethoxy) and p-trifluoromethylbenzyloxy (4-trifluoromethylphenylmethoxy); heteroaryloxy groups; sulfonyl groups, such as trifluoromethanesulfonyl, methanesulfonyl, and p-toluenesulfonyl; nitro, nitrosyl; mercapto; sulfanyl groups, such as methylsulfanyl, ethylsulfanyl and propylsulfanyl; cyano; amino groups, such as amino, methylamino, dimethylamino, ethylamino, and diethylamino; and carboxyl. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

In choosing the compounds of the present invention, one of ordinary skill in the art will recognize that the various substituents, i.e. $R_1$, $R_2$, etc. are to be chosen in conformity with well-known principles of chemical structure connectivity.

The various R groups attached to the aromatic rings of the compounds disclosed herein may be added to the rings by standard procedures, for example those set forth in Advanced Organic Chemistry: Part B: Reaction and Synthesis, Francis Carey and Richard Sundberg, (Springer) 5th ed. Edition. (2007), the content of which is hereby incorporated by reference.

The compounds used in the method of the present invention may be prepared by techniques well know in organic synthesis and familiar to a practitioner ordinarily skilled in the art. However, these may not be the only means by which to synthesize or obtain the desired compounds.

The compounds used in the method of the present invention may be prepared by techniques described in Vogel's Textbook of Practical Organic Chemistry, A. I. Vogel, A. R. Tatchell, B. S. Furnis, A. J. Hannaford, P. W. G. Smith, (Prentice Hall) $5^{th}$ Edition (1996), March's Advanced Organic Chemistry: Reactions, Mechanisms, and Structure, Michael B. Smith, Jerry March, (Wiley-Interscience) $5^{th}$ Edition (2007), and references therein, which are incorporated by reference herein. However, these may not be the only means by which to synthesize or obtain the desired compounds.

Another aspect of the invention comprises a compound used in the method of the present invention as a pharmaceutical composition.

As used herein, the term "pharmaceutically active agent" means any substance or compound suitable for administration to a subject and furnishes biological activity or other direct effect in the treatment, cure, mitigation, diagnosis, or prevention of disease, or affects the structure or any function of the subject. Pharmaceutically active agents include, but are not limited to, substances and compounds described in the Physicians' Desk Reference (PDR Network, LLC; 64th edition; Nov. 15, 2009) and "Approved Drug Products with Therapeutic Equivalence Evaluations" (U.S. Department Of Health And Human Services, $30^{th}$ edition, 2010), which are hereby incorporated by reference. Pharmaceutically active agents which have pendant carboxylic acid groups may be modified in accordance with the present invention using standard esterification reactions and methods readily available and known to those having ordinary skill in the art of chemical synthesis. Where a pharmaceutically active agent does not possess a carboxylic acid group, the ordinarily skilled artisan will be able to design and incorporate a carboxylic acid group into the pharmaceutically active agent where esterification may subsequently be carried out so long as the modification does not interfere with the pharmaceutically active agent's biological activity or effect.

The compounds used in the method of the present invention may be in a salt form. As used herein, a "salt" is a salt of the instant compounds which has been modified by making acid or base salts of the compounds. In the case of compounds used to treat an infection or disease caused by a pathogen, the salt is pharmaceutically acceptable. Examples of pharmaceutically acceptable salts include, but are not limited to, mineral or organic acid salts of basic residues such as amines; alkali or organic salts of acidic residues such as phenols. The salts can be made using an organic or inorganic acid. Such acid salts are chlorides, bromides, sulfates, nitrates, phosphates, sulfonates, formates, tartrates, maleates, malates, citrates, benzoates, salicylates, ascorbates, and the like. Phenolate salts are the alkaline earth metal salts, sodium, potassium or lithium. The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately reacting a purified compound of the invention in its free base or free acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts and the like. (See, e.g., Serge et al. (1977) "Pharmaceutical Salts", *J. Pharm. Sci.* 66:1-19).

As used herein, "treating" means preventing, slowing, halting, or reversing the progression of a disease or infection. Treating may also mean improving one or more symptoms of a disease or infection.

The compounds used in the method of the present invention may be administered in various forms, including those detailed herein. The treatment with the compound may be a component of a combination therapy or an adjunct therapy, i.e. the subject or patient in need of the drug is treated or given another drug for the disease in conjunction with one or more of the instant compounds. This combination therapy can be sequential therapy where the patient is treated first with one drug and then the other or the two drugs are given simultaneously. These can be administered independently by the same route or by two or more different routes of administration depending on the dosage forms employed.

As used herein, a "pharmaceutically acceptable carrier" is a pharmaceutically acceptable solvent, suspending agent or vehicle, for delivering the instant compounds to the animal or human. The carrier may be liquid or solid and is selected with the planned manner of administration in mind. Liposomes are also a pharmaceutically acceptable carrier.

The dosage of the compounds administered in treatment will vary depending upon factors such as the pharmacodynamic characteristics of a specific chemotherapeutic agent and its mode and route of administration; the age, sex, metabolic rate, absorptive efficiency, health and weight of the recipient; the nature and extent of the symptoms; the kind of concurrent treatment being administered; the frequency of treatment with; and the desired therapeutic effect.

A dosage unit of the compounds used in the method of the present invention may comprise a single compound or mixtures thereof with additional antibacterial agents. The compounds can be administered in oral dosage forms as tablets, capsules, pills, powders, granules, elixirs, tinctures, suspensions, syrups, and emulsions. The compounds may also be administered in intravenous (bolus or infusion), intraperitoneal, subcutaneous, or intramuscular form, or introduced directly, e.g. by injection, topical application, or other methods, into or onto a site of infection, all using dosage forms well known to those of ordinary skill in the pharmaceutical arts.

The compounds used in the method of the present invention can be administered in admixture with suitable pharmaceutical diluents, extenders, excipients, or carriers (collectively referred to herein as a pharmaceutically acceptable carrier) suitably selected with respect to the intended form of administration and as consistent with conventional pharmaceutical practices. The unit will be in a form suitable for oral, rectal, topical, intravenous or direct injection or parenteral administration. The compounds can be administered alone or mixed with a pharmaceutically acceptable carrier. This carrier can be a solid or liquid, and the type of carrier is generally chosen based on the type of administration being used. The active agent can be co-administered in the form of a tablet or capsule, liposome, as an agglomerated powder or in a liquid form. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents, flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms may also include minerals and other materials to make them compatible with the type of injection or delivery system chosen.

Techniques and compositions for making dosage forms useful in the present invention are described in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol. 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modem Pharmaceutics Drugs and the Pharmaceutical Sciences, Vol 40 (Gilbert S. Banker, Christopher T. Rhodes, Eds.). All of the aforementioned publications are incorporated by reference herein.

Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol and the like. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds used in the method of the present invention may also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines. The compounds may be administered as components of tissue-targeted emulsions.

The compounds used in the method of the present invention may also be coupled to soluble polymers as targetable drug carriers or as a prodrug. Such polymers include polyvinylpyrrolidone, pyran copolymer, polyhydroxylpropylmethacrylamide-phenol, polyhydroxyethylaspartamidephenol, or polyethyleneoxide-polylysine substituted with palmitoyl residues. Furthermore, the compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Gelatin capsules may contain the active ingredient compounds and powdered carriers, such as lactose, starch, cellulose derivatives, magnesium stearate, stearic acid, and the like. Similar diluents can be used to make compressed tablets. Both tablets and capsules can be manufactured as immediate release products or as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

For oral administration in liquid dosage form, the oral drug components are combined with any oral, non-toxic, pharmaceutically acceptable inert carrier such as ethanol, glycerol, water, and the like. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents.

Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol. Suitable pharmaceutical carriers are described in Remington's Pharmaceutical Sciences, Mack Publishing Company, a standard reference text in this field.

The compounds used in the method of the present invention may also be administered in intranasal form via use of suitable intranasal vehicles, or via transdermal routes, using those forms of transdermal skin patches well known to those of ordinary skill in that art. To be administered in the form of a transdermal delivery system, the dosage administration will generally be continuous rather than intermittent throughout the dosage regimen.

Parenteral and intravenous forms may also include minerals and other materials to make them compatible with the type of injection or delivery system chosen.

The compounds and compositions of the present invention can be administered in oral dosage forms as tablets, capsules, pills, powders, granules, elixirs, tinctures, suspensions, syrups, and emulsions. The compounds may also be administered in intravenous (bolus or infusion), intraperitoneal, subcutaneous, or intramuscular form, or introduced directly, e.g. by topical administration, injection or other methods, to the afflicted area, such as a wound, including ulcers of the skin, all using dosage forms well known to those of ordinary skill in the pharmaceutical arts.

Specific examples of pharmaceutical acceptable carriers and excipients that may be used to formulate oral dosage forms of the present invention are described in U.S. Pat. No. 3,903,297 to Robert, issued Sep. 2, 1975. Techniques and compositions for making dosage forms useful in the present invention are described-in the following references: 7 Modem Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Harwood Books in the Biological Sciences. Series in Pharmaceutical Technology; J. G. Hardy, S. S. Davis, Clive G. Wilson, Eds.); Modem Pharmaceutics Drugs and the Pharmaceutical Sciences, Vol 40 (Gilbert S. Banker, Christopher T. Rhodes, Eds.). All of the aforementioned publications are incorporated by reference herein.

The term "prodrug" as used herein refers to any compound that when administered to a biological system generates the compound of the invention, as a result of spontaneous chemical reaction(s), enzyme catalyzed chemical reaction(s), photolysis, and/or metabolic chemical reaction(s). A prodrug is thus a covalently modified analog or latent form of a compound of the invention.

The active ingredient can be administered orally in solid dosage forms, such as capsules, tablets, powders, and chewing gum; or in liquid dosage forms, such as elixirs, syrups, and suspensions, including, but not limited to, mouthwash and toothpaste. It can also be administered parentally, in sterile liquid dosage forms.

Solid dosage forms, such as capsules and tablets, may be enteric coated to prevent release of the active ingredient compounds before they reach the small intestine. Materials that may be used as enteric coatings include, but are not limited to, sugars, fatty acids, waxes, shellac, cellulose acetate phthalate (CAP), methyl acrylate-methacrylic acid copolymers, cellulose acetate succinate, hydroxy propyl methyl cellulose phthalate, hydroxy propyl methyl cellulose acetate succinate (hypromellose acetate succinate), polyvinyl acetate phthalate (PVAP), and methyl methacrylate-methacrylic acid copolymers.

The compounds and compositions of the invention can be coated onto stents for temporary or permanent implantation into the cardiovascular system of a subject.

The compounds of the present invention can be synthesized according to general Schemes. Variations on the following general synthetic methods will be readily apparent to those skilled in the art and are deemed to be within the scope of the present invention.

Each embodiment disclosed herein is contemplated as being applicable to each of the other disclosed embodiments. Thus, all combinations of the various elements described herein are within the scope of the invention.

This invention will be better understood by reference to the Experimental Details which follow, but those skilled in the art will readily appreciate that the specific experiments detailed are only illustrative of the invention as described more fully in the claims which follow thereafter.

Experimental Details

Recombinant HDAC1 and HDAC6 are used to evaluate the selective inhibitory potency of each compound. Cell based assays: Normal cells (Human Foreskin Fibroblast cells), LNCaP (human prostate cancer cells), MCF-7 (human breast cancer cells, A549 (human adenocarcinoma of lung cells) and ARP-1 (human multiple myeloma cells) are used in these assays. Cells were cultured for up to 72 hr without and with the potential HDAC6-selective inhibitor. SAHA was used as a control. Cell number and cell viability were determined by enumeration. Proteins were extracted from cells and assayed for accumulation of acetylated tubulin and acetylated histones. All methods are described in Namdar et al., *PNAS*, 2010, 107:20003-8. In vivo animal studies: Potential HDAC6 inhibitor compounds are further assayed by administration to mice for up to 5 days with daily injections. Animals are sacrificed and tissues are analyzed for accumulation of acetylated tubulin and acetylated histones.

8-Aminoquinoline, aniline, glycolaldehyde dimer, sodium triacetoxyborohydride, tert-butylchlorodimethylsilane (TBDMS-Cl), potassium cyanide, $NH_2OH$, trifluoroacetic acid (TFA), dichloroethane (DCE), dichloromethane (DCM), 1-Ethyl-3-(3-dimethyllaminopropyl)carbodiimide hydrochloride (EDC), sodium sulfate (anhydrous), calcium hypochlorite, molecular sieves (4 Å), $NH_4Cl$, NaCl, MeOH, $NaHCO_3$, THF, hydrochloric acid, acetic acid, $CDCl_3$, $CD_3OD$, and hexanes were used as received without further purification. Purification of product mixtures was carried out by column using silica gel with 40-60 Å particle size or preparative chromatography using silica gel 60F 254 TLC-plates. TLC was carried out using silica gel 60F 254 TLC-plates. Proton NMR data were acquired at 400 MHz and $^{13}C$ NMR data were acquired at 100.6 MHz.

Those having ordinary skill in the art of organic synthesis will appreciate that modifications to general procedures and synthetic routes contained in this application can be used to yield additional derivatives and structurally diverse compounds. Suitable organic transformations are described in March's Advanced Organic Chemistry: Reactions, Mechanisms, and Structure (Wiley-Interscience; 6th edition, 2007), the content of which is hereby incorporated by reference.

Example 1. Synthesis of Compound 8

HDAC inhibitor 8 was prepared according to the protocols shown in Scheme 1 and Scheme 2. Methyl ester 5 was prepared by treatment of mesylate 2 with 2-(tert-butyldimethylsiloxy) ethanamine 4 in the presence of triethylamine. Amine 5 was coupled to 2-phenylacetyl chloride to form amide 7. The methyl ester of 7 was converted directly, using aqueous hydroxylamine, to the corresponding hydroxamic acid, which was deprotected with 2% aqueous HCl to afford compound 8.

Scheme 1.

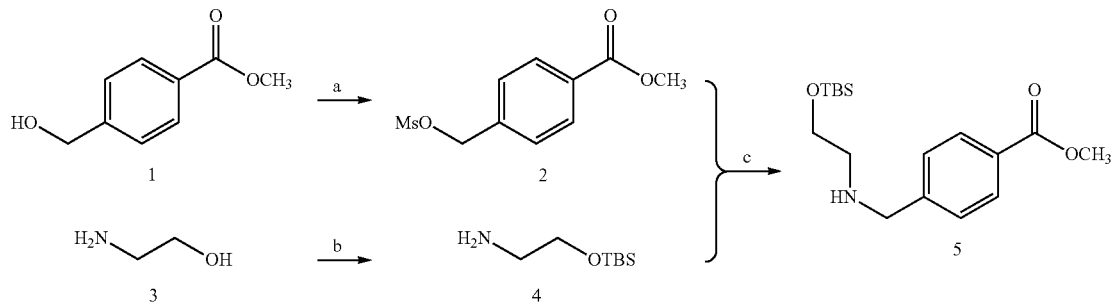

Scheme 1: Reagents and contitions: a) Et₃N, MsCl, CH₂Cl₂, 0° C. - rt; b) Imidazole, TBSCl, CH₂Cl₂, 0° C. - rt; c) 2, 4, Et₃N, DMF, rt.

Methyl 4-(((methylsulfonyl)oxy)methyl)benzoate (2)

Triethylamine (1.3 mL, 9.0 mmol) was added drop wise over 1 min to a solution of methanesulfonyl chloride (0.55 mL, 7.2 mmol), methyl 4-(hydroxymethyl)-benzoate (1.0 g, 6.0 mmol), and $CH_2Cl_2$ (40 mL) at 0° C. The resulting solution was allowed to warm to rt and maintained for 1 hr. Water (2 ml) was added and the mixture stirred for 15 min. The organic layer was extracted with $NaHCO_3$ (10 ml×2), $H_2O$ (10 mL×2), and brine (10 mL). The resulting solution was dried ($MgSO_4$), filtered, and concentrated to yield a white solid. $^1H$ NMR (400 MHz, $CDCl_3$) δ 3.13 (s, 3H), 3.89 (s, 3H), 4.9 (s, 2H), 7.52 (d, J=8.4 Hz, 2H), 8.06 (d, J=8.4 Hz, 2H); $^{13}C$ NMR (100 MHz, $CDCl_3$) δ 166.1, 137.2, 131.5, 130.1, 127.5, 75.0, 52.3, 39.4; $[M+H]^+$=245.5 (APCI+).

2-((tert-butyldimethylsilyl)oxy)ethan-1-amine (4)

A solution of tert-butyldimethylchlorosilane (3.6 g, 24 mmol) and dichloromethane (10 mL) was added drop wise over 3 min to a stirred solution of ethanolamine (1.22 g, 20 mmol), imidazole (2.04 g, 30 mmol), and dichloromethane (20 mL) at room temperature, and the resulting mixture was stirred at room temperature for 1 h., water (20 mL) was added, and the phases were separated. The aqueous phase was extracted with dichloromethane (2×20 mL), and the combined organic phases were dried ($MgSO_4$), filtered and concentrated in vacuo to give the title compound (3.50 g, 100%) as pale yellow oil. $^1H$ NMR (400 MHz, $CDCl_3$) δ 3.64 (t, J=5.0, 2H,), 3.05 (br s, 2H), 2.80 (t, J=5.0, 2H), 0.90 (s, 9H), 0.06 (s, 6H); $^{13}C$ NMR (100 MHz, $CDCl_3$) δ 64.7, 44.1, 25.9, 18.3, −3.4; $[M+H]^+$=176.6 (APCI+).

Methyl 4-(((2-((tert-butyldimethylsilyl)oxy)ethyl) amino) methyl) benzoate (5)

2-(tert-Butyldimethylsiloxy)ethanamine 4, (1.54 g, 8.64 mmol) was added to a solution of 4-methanesulfonyloxymethylbenzoic acid methyl ester (1.76 g, 7.2 mmol) and triethylamine (0.98 mL, 7.2 mmol) in DMF (10 mL), and then the reaction mixture was stirred at room temperature for 2 hours. Saturated aq $NaHCO_3$ solution (150 mL) was added, and then the whole reaction mixture was extracted with chloroform (100 mL×3). The organic layer was dried. Evaporation and purification by silica gel column chromatography (EtOAc:n-hexanes, 1:4) gave 5 as a yellowish oil (1.82 g, 78% yield): $^1H$ NMR (400 MHz, $CDCl_3$): 7.94 (d, J=8.4 Hz, 2H), 7.34 (d, J=8.0 Hz, 2H), 3.85 (s, 3H), 3.81 (s, 2H), 3.68 (t, J=2.67 (t, J=5.2 Hz, 2H,) 0.76 (s, 9H), δ 0.02 (s, 6H); $^{13}C$ NMR ($CHCl_3$, 100 MHz): δ 167.1, 136.8, 132.5, 130.3, 127.5, 75.0, 64.7, 52.3, 44.1, 25.9, 18.8, −3.4; $[M+H]^+$=324.2 (APCI+).

Scheme 2.

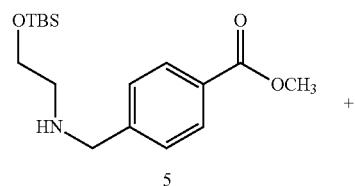

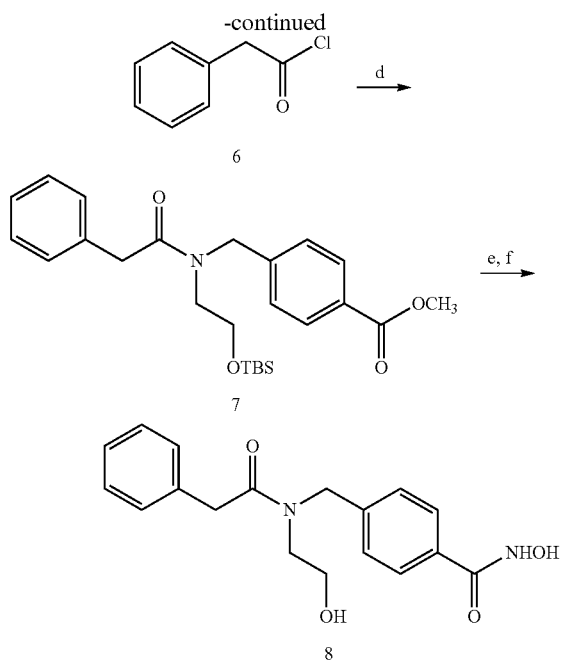

Scheme 2: Reagents and conditions: d) 5, 6, $Et_3N$, $CH_2Cl_2$, 0° C. - rt; e) 50% (w/w) aq. $NH_2OH$, MeOH, rt; f) 2% aq. HCl, MeOH, 0° C. - rt.

Methyl 4-((N-(2-((tert-butyldimethylsilyl)oxy) ethyl)-2-phenyl acetamido)methyl)benzoate (7)

2-phenylacetyl chloride (0.44 mL, 3.3 mmol) was added drop wise to a solution of 5 (0.89 g, 2.75 mmol) in 8 mL dry dichloromethane containing triethylamine (0.7 mL, 4.95 mmol) at 0° C. The resulting solution was allowed to warm to rt and stirred for 4 hr. After completion of the reaction (by TLC), added 30 mL dichloromethane and washed with sat. ammonium chloride (30 mL×2) and brine (30 mL×2). The organic layer was dried ($MgSO_4$), filtered, and concentrated in vacuo. The Crude compound was purified on silica gel column (EtOAc:Hexanes, 1:5) to give the compound 7 (0.87 g, 72%). $^1H$ NMR ($CHCl_3$, 400 MHz): δ 7.91 (d, J=8.2, Hz, 2H), 7.38 (m, 3H), 7.15 (m, 4H), 3.91 (s, 3H), 3.80 (m, 4H), 3.50 (s, 2H), 0.85 (s, 9H), 0.02 (s, 6H); $^{13}C$ NMR ($CHCl_3$, 100 MHz): δ 170.2, 167.0, 142.9, 140.8, 129.6, 129.5, 129.1, 128.6, 128.5, 128.0, 60.1, 52.1, 52.0, 41.4, 39.9, 25.8, 18.2, −5.4; $[M+H]^+$=442.6 (APCI+).

N-hydroxy-4-((N-(2-hydroxyethyl)-2-phenylacetamido) methyl) benzamide (8)

Hydroxylamine (0.5 mL, 50% water solution) was added to a solution of 7, (500 mg, 1.13 mmol) in methanol (5 mL). Reaction mixture was treated with cat. amount of KCN (~0.5 mg) and stirred at room temperature in argon atmosphere for 16 h. Then solution was acidified by $NH_4Cl$/HCl solution to pH~4.5. The mixture was diluted with mixed solvent ($CHCl_3$:i-PrOH=4:1, 10 mL) and washed with sat. $NH_4Cl$. The organic layer was dried (anhydrous sodium sulfate) and concentrated in vacuo. Crude material was dissolved in MeOH (8 mL) and added 4% (v/v) HCl in MeOH (8 mL) drop wise at 0° C. The reaction mixture was stirred at room temperature for 3 hrs. Once the starting material is completely consumed, added solid NaHCO3 (~100 mg) to neutralize excess HCl. Organics was filtered, dried over Na2SO4 and evaporated in vacuo. Crude material was purified on silica gel column (MeOH/CH$_2$Cl$_2$=1/10) to give the titled compound 8. (120 mg, 32.2%) $^1$H NMR (CD$_3$OD, 400 MHz): δ 7.75-7.69 (m, 2H), 7.36-7.22 (m, 7H), 4.83 (s, 1H), 4.75 (s, 1H), 3.96 (s, 1H), 3.78 (s, 1H), 3.72-3.67 (m, 2H), 3.52 (m, 2H); $^{13}$C NMR (CD$_3$OD, 100 MHz) δ 173.2, 173.1, 166.5, 166.3, 141.6, 140.9, 135.2, 134.8, 131.4, 131.1, 128.7, 128.6, 128.3, 127.4, 127.3, 127.0, 126.5, 59.3, 59.1, 52.4, 49.6, 48.7, 48.3, 40.2, 39.9; [M+H]=329.1 (APCI+); HRMS calcd for C$_{18}$H$_{21}$N$_2$O$_4$ [M+H]$^+$ 329.1501, found 329.1494.

Example 2. Synthesis of Compound 11

HDAC inhibitor 11 was prepared according to the protocols shown in Scheme 3. Amine 5 was coupled to benzoyl chloride to form amide 10. The methyl ester of 10 was converted directly, using aqueous hydroxylamine, to the corresponding hydroxamic acid, which was deprotected with 2% aqueous HCl to afford compound 11.

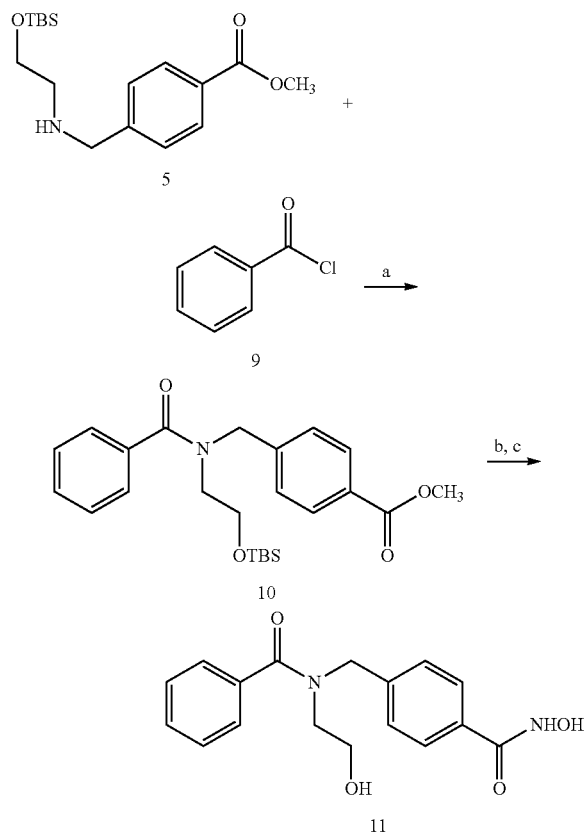

Reagents and conditions: a) 5, 7, Et$_3$N, CH$_2$Cl$_2$, 0° C. - rt;
b) 50% (w/w) aq. NH$_2$OH, MeOH, rt; f) 2% aq. HCl, MeOH, 0° C. - rt.

Methyl 4-((N-(2-((tert-butyldimethylsilyl)oxy)ethyl) benzamido) methyl)benzoate (10)

Benzoyl chloride (0.73 mL, 6.31 mmol) was added drop wise to a solution of 5 (1.7 g, 5.26 mmol) in 15 mL dry dichloromethane containing triethylamine (1.3 mL, 9.5 mmol) at 0° C. Then the reaction mixture is allowed to reach room temperature and stirred for 4 hrs. After completion of the reaction (by TLC), added 30 mL dichloromethane and washed with sat. ammonium chloride (30 mL×2) followed by sat. sodium chloride (30 mL×2). The organic layer was dried with anhydrous NaSO$_4$, filtered, and removed under vacuum. Crude compound was purified on silica gel column (EtOAc:Hexanes, 1:5) to give the compound 10 (0.92 g, 70%). $^1$H NMR (CHCl$_3$, 400 MHz): δ 7.91 (d, J=8.2, Hz, 2H), 7.38 (m, 3H), 7.15 (m, 4H), 3.91 (s, 3H), 3.80 (m, 4H), 3.60 (s, 2H), 0.85 (s, 9H), 0.02 (s, 6H); $^{13}$C NMR (CHCl$_3$, 100 MHz): δ 171.2, 168.0, 142.4, 140.8, 129.6, 129.5, 129.1, 128.6, 128.5, 128.0, 54.1, 53.0, 41.4, 39.9, 25.8, 18.2, −5.4; [M+H]$^+$=428.4 (APCI+).

N-hydroxy-4-((N-(2-hydroxyethyl)-2-benzamido) methyl)benzamide (11)

Hydroxylamine (0.5 mL, 50% water solution) was added to a solution of 10, (500 mg, 1.13 mmol) in methanol (5 mL). Reaction mixture was treated with cat. amount of KCN (~0.5 mg) and stirred at room temperature in argon atmosphere for 16 h. Then solution was acidified by NH$_4$Cl/HCl solution to pH~4.5. The mixture was diluted with mixed solvent (CHCl$_3$:i-PrOH=4:1, 10 mL) and washed with sat. NH$_4$Cl. The organic layer was dried (anhydrous sodium sulfate) and concentrated in vacuo. Crude material was dissolved in MeOH (8 mL) and added 4% (v/v) HCl in MeOH (8 mL) drop wise at 0° C. The reaction mixture was stirred at room temperature for 3 hrs. Once the starting material is completely consumed, added solid NaHCO$_3$ (~100 mg) to neutralize excess HCl. Organics was filtered, dried over Na2SO4 and evaporated in vacuo. Crude material was purified on silica gel column (MeOH:CH$_2$Cl$_2$=1:10) to give the titled compound 11. (140 mg, 38.1%) $^1$H NMR (CD$_3$OD, 400 MHz): δ 7.80-7.75 (m, 2H), 7.52-7.45 (m, 6H), 7.30 (m, 1H), 4.73 (s, 1H), 3.84 (s, 1H), 3.61 (s, 2H), 3.42-3.39 (m, 1H); $^{13}$C NMR (CD$_3$OD, 100 MHz) δ 173.5, 166.5, 141.4, 140.8, 136.1, 135.9, 131.5, 131.2, 129.4, 128.3, 127.6, 127.3, 127.2, 126.8, 126.6, 126.2, 59.1, 58.7, 53.6, 48.3; [M+H]$^+$=315.1 (APCI+); HRMS calcd for C$_{17}$H$_{19}$N$_2$O$_4$ [M+H]$^+$ 315.1345. found 315.1337.

Example 3. Synthesis of Compound 23

HDAC inhibitor 23 was prepared according to the protocols shown in Schemes 4 and 5. Amine 20 was coupled to acid 18 to form amide 21. The methyl ester of 21 was converted directly, using aqueous hydroxylamine, to the corresponding hydroxamic acid, which was deprotected with 2% aqueous HCl to afford compound 23.

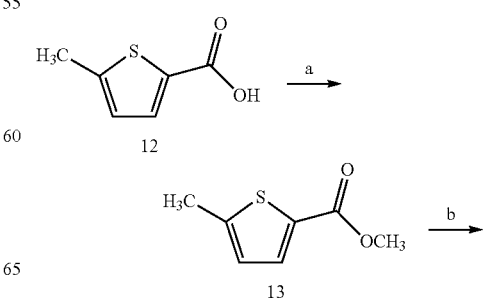

Scheme 4.

-continued

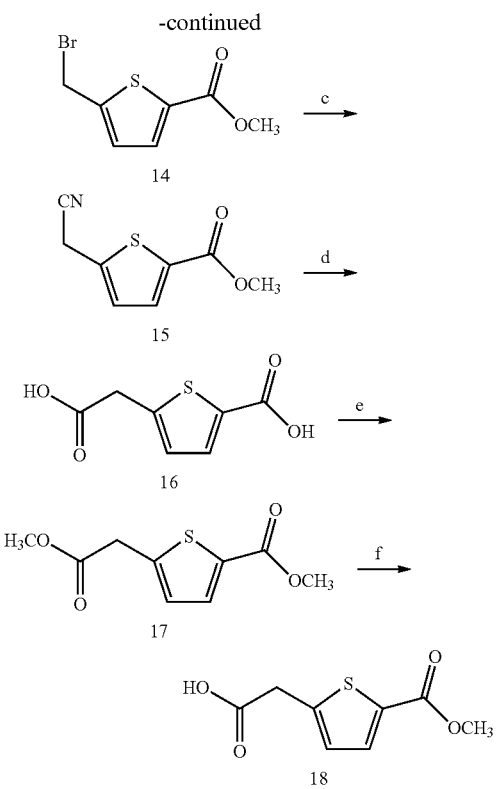

Reagents and contidions; a) MeOH/cat. H₂SO₄ 70° C. 6 h; b) NBS, (PhCO₂)₂, CCl4, 80° C., 12 h; c) NaCN, DMF/H2O, 70° C., 4 h; d) aq NaOH (6N), MeOH, 90° C. 12 h; e) MeOH/cat. H₂SO₄ 90° C. 18 h; f) MeOH, H₂O, K₂CO₃, rt, 4 h.

Methyl 5-methyl-2-thiophenecarboxylate (13)

5-Methyl-thiophene-2-carboxylic acid (5 g, 35 mmol) was refluxed in H₂SO₄ in MeOH (2 M) for 6 h. The reaction was neutralized with NaOH (10 N) at 0° C., and the methyl ester was extracted with DCM affording 4.85 g (89%) of 5-methylthiophene-2-carboxylic acid methyl ester. ¹H NMR (CHCl₃, 400 MHz): δ 7.78 (d, J=3.8, 1H), 6.82 (d, J=3.8, 1H), 3.90 (s, 3H), 2.21 (s, 3H); ¹³C NMR (CHCl₃, 100 MHz): δ 162.1, 144.2, 137.5, 132.2, 129.2, 53.0, 18.9; [M+H]⁺=157.12 (APCI+).

Methyl 5-(bromomethyl)thiophene-2-carboxylate (14)

The methyl ester 13, (2.4 g, 15.5 mmol) was refluxed in CCl₄ in the presence of NBS (3 g, 17 mmol) and benzoyl peroxide (121 mg, 0.03 equiv) for 12 h. The reaction was cooled to 0° C. and filtered. Organics was filtered, dried over Na2SO4 and evaporated in vacuo. Crude material was purified on silica gel column (EtOAc:Hexanes=1:5) to give the titled compound 14. (2.9 g, 82%). ¹H NMR (CHCl₃, 400 MHz): δ 7.64 (d, J=3.6, 1H), 7.10 (m, 1H), 3.90 (s, 3H), 3.89 (s, 3H); ¹³C NMR (CHCl₃, 100 MHz): δ 162.4, 149.8, 135.5, 130.2, 124.8, 52.4, 23.4; [M+H]⁺=235.1 (APCI+).

Methyl 5-(cyanomethyl)thiophene-2-carboxylate (15)

A solution of NaCN (787 mg, 16.0 mmol) in water (2 mL) was added drop wise to a solution of Methyl 5-(bromomethyl)thiophene-2-carboxylate 14, (2.6 g, 11.06 mmol) in DMF (18 mL) at 0° C. in argon atmosphere. The reaction mixture was stirred for 4 hrs. After completion of reaction (TLC) added saturated ammonium chloride solution (50 mL) and extracted with dichloromethane (30 mL×3). Organics was combined, dried over Na₂SO₄ and evaporated in vacuo. Crude material was purified on silica gel column (EtOAc:Hexanes=1:4) to give the titled compound 15. (1.1 g, 55%). ¹H NMR (CHCl₃, 400 MHz): δ 7.62 (d, J=3.6, 1H), 7.10 (m, 1H), 4.31 (s, 2H), 3.89 (s, 3H); ¹³C NMR (CHCl₃, 100 MHz): δ 164.4, 138.6, 136.2, 133.2, 127.1, 62.4, 20.4, 17.0; [M+H]⁺=182.3 (APCI+).

5-(carboxymethyl)thiophene-2-carboxylic acid (16)

A solution of methyl 5-(cyanomethyl)thiophene-2-carboxylate 15, (500 mg, 2.76 mmol) in 6M Sodium hydroxide (10 mL) and methanol (10 mL) was heated at 90° C. overnight. After concentrating the reaction mixture, the aqueous layer was washed with dichloromethane (20 mL×2), then acidified to pH~3 with 12M HCl. The aqueous solution was extracted with ethyl acetate (20 mL×2). Organics was combined, dried over Na₂SO₄ and evaporated in vacuo to give titled compound 16. (650 mg, 80%). ¹H NMR (CHCl₃, 400 MHz): δ 7.70 (d, J=3.6, 1H), 6.91 (m, 1H), 4.03 (s, 2H); ¹³C NMR (CHCl₃, 100 MHz): δ 178.4, 164.3, 145.5, 138.3, 132.2, 127.5, 38.5; [M+H]⁺=187.2 (APCI+).

Methyl 5-(2-methoxy-2-oxoethyl)thiophene-2-carboxylate (17)

A solution of 5-(carboxymethyl)thiophene-2-carboxylic acid 16, (500 mg, 2.68 mmol) and H₂SO₄ (2 mL) in methanol (20 mL) was heated at 90° C. overnight. After concentrating the reaction mixture, the crude was taken into EtOAc (30 mL) and washed with sat. NaHCO₃ (30 mL). Then the organic layer was dried over Na₂SO₄ and evaporated in vacuo. Crude material was purified on silica gel column (EtOAc:Hexanes=1:6) to give the title compound 17. (525 mg, 90%). ¹H NMR (CHCl₃, 400 MHz): δ 7.61 (d, J=3.6, 1H), 7.01 (m, 1H), 3.91 (s, 3H), 3.80 (s, 2H), 3.62 (s, 3H); ¹³C NMR (CHCl₃, 100 MHz): δ 172.4, 163.5, 141.5, 137.3, 130.2, 125.5, 53.5, 53.0, 37.5; [M+H]⁺=215.4 (APCI+).

2-(5-(methoxycarbonyl)thiophen-2-yl)acetic acid (18)

A solution of methyl 5-(2-methoxy-2-oxoethyl)thiophene-2-carboxylate 17, (500 mg, 2.33 mmol) and K₂CO₃ (572 mg, 3.49 mmol) in water/methanol mixture (15 mL, 1:1) was stirred at room temperature 4 hrs. After concentrating the reaction mixture to 5 mL diluted with water (20 mL). Then the aqueous layer was washed with dichloromethane (20 mL×2), and acidified to pH~3 with 12M HCl. The aqueous solution was extracted with ethyl acetate (20 mL×2). Organics was combined, dried over Na₂SO₄ and evaporated in vacuo to give titled compound 18. (400 mg, 85%). ¹H NMR (CHCl₃, 400 MHz): δ 7.60 (d, J=3.6, 1H), 6.80 (m, 1H), 3.80 (s, 2H), 3.75 (s, 3H); ¹³C NMR (CHCl₃, 100 MHz): δ 178.1, 163.3, 145.1, 131.2, 126.5, 53.4, 37.5; [M+H]⁺=201.2 (APCI+).

Scheme 5.

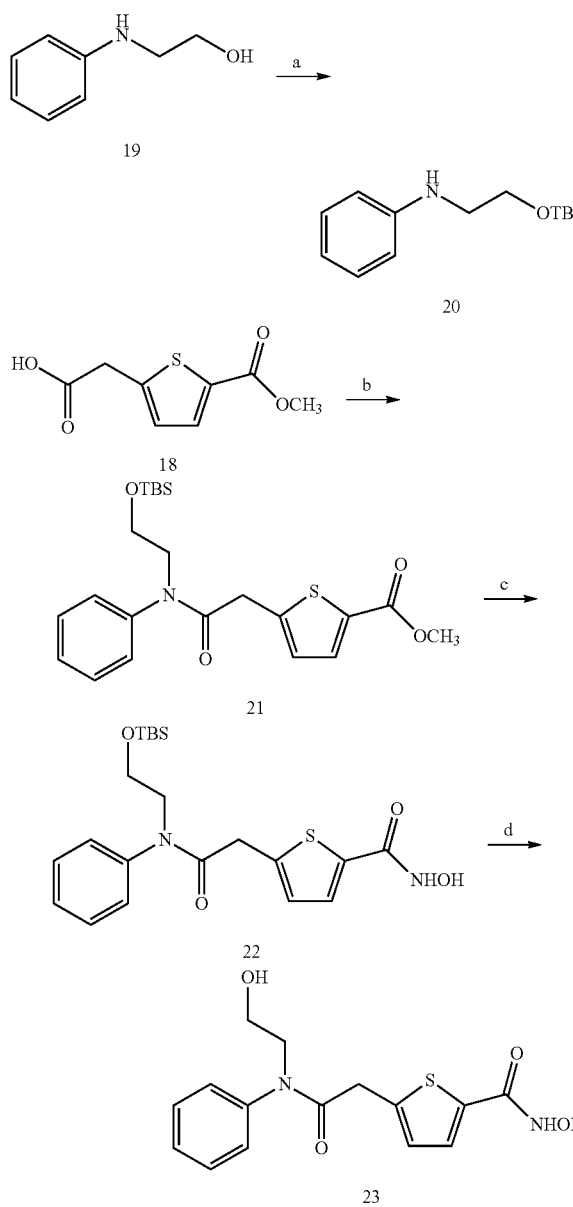

Reagents and conditions; a) Imidazole, TBSCl, CH₂Cl₂, rt; b) 20, EDCI, Et₃N, CH₂Cl₂, rt, 18 h; 50%; ci) (w/w) aq. NH₂OH, MeOH, rt; d) 2% aq. HCl, MeOH, 0° C. - rt, 3 h.

N-(2-((tert-butyldimethylsilyl)oxy)ethyl)aniline (20)

TBDMS-Cl (1.28 g, 6.02 mmol) and imidazole (1.45 g, 21.86 mmol) was added to a solution containing 2-(phenylamino)ethanol 19, (1.00 g, 7.29 mmol) in CH$_2$Cl$_2$ (10 mL). The reaction mixture was stirred at room temperature in argon atmosphere for 3 h. Then the reaction was quenched with sat. NH$_4$Cl. and washed with water (10 mL×2) and brine (10 mL×2). The organic layer was dried (anhydrous sodium sulfate) and concentrated in vacuo. The crude product was chromatographed on silica gel (Hexanes/EtOAc, 7:1) to yield target compound 20. Yield 1.689 g, 92%. R$_f$=0.60, $^1$H NMR (CHCl$_3$, 400 MHz): δ 7.22 (dd, J=8.8, 7.4 Hz, 2H), 6.76 (t, J=7.4 Hz, 1H), 6.68 (d, J=8.8, 2H), 4.09 (br s, 1H), 3.86 (t, J=5.2 Hz, 2H), 3.26 (t, J=5.2 Hz, 2H), 0.95 (s, 9H), 0.11 (s, 6H); $^{13}$C NMR (CHCl$_3$, 100 MHz): δ 148.4, 129.2, 117.5, 113.2, 61.6, 46.0, 25.9, 18.3, −5.3; [M+H]$^+$=252.12 (APCI+).

Methyl 5-(2-((2-((tert butyldimethylsilyl)oxy)ethyl)(phenyl) amino)-2-oxoethyl)thiophene-2-carboxylate) (21)

EDCI (291.0 mg, 1.52 mmol) was added to a solution containing N-(2-((tert-butyldimethyl silyl) oxy)ethyl)aniline 20, (390 mg, 1.60 mmol) and 2-(5-(methoxycarbonyl)thiophen-2-yl)acetic acid 18, (260 mg, 1.30 mmol) in CH$_2$Cl$_2$ (5 mL). The reaction mixture was stirred overnight at room temperature in argon atmosphere. After completion of reaction the reaction mixture was diluted with mixed solvent (CHCl$_3$:i-PrOH=4:1, 10 mL) and washed with sat. NH$_4$Cl. The organic layer was dried (anhydrous sodium sulfate) and concentrated in vacuo. The crude product was chromatographed on silica gel (Hexanes/EtOAc, 7:1) to yield title compound 21. (378 mg, 67%). $^1$H NMR (CHCl$_3$, 400 MHz): δ 7.91 (d, J=8.2, Hz, 2H), 7.61 (d, J=3.6, 1H), 7.38 (m, 3H), 7.15 (m, 2H), 3.91 (s, 3H), 3.80 (m, 4H), 3.50 (s, 2H), 0.85 (s, 9H), 0.02 (s, 6H); $^{13}$C NMR (CHCl$_3$, 100 MHz): δ 170.2, 167.0, 145.1, 131.5, 129.5, 129.1, 128.6, 128.5, 127.5, 127.0, 60.1, 52.1, 52.0, 41.4, 25.8, 18.2, −5.4; [M+H]$^+$=434.84 (APCI+).

5-(2-((2-(((tert-butyldimethylsilyl)oxy) ethyl) (phenyl) amino)-2-oxoethyl)-N-hydroxythiophene-2-carboxamide (22)

Hydroxylamine (0.5 mL, 50% water solution) was added to a solution containing methyl 5-(2-((2-((tert-butyldimethylsilyl)oxy)ethyl) (phenyl)amino)-2-oxoethyl)thiophene-2-carboxylate) 21, (250 mg, 0.576 mmol) in THF/MeOH (1:1, 2 mL). Reaction mixture was treated with catalytic amount of KCN (~0.5 mg) and stirred at room temperature in argon atmosphere for 16 h. Then solution was acidified by NH$_4$Cl/HCl solution to pH~4. The mixture was diluted with mixed solvent (CHCl$_3$:i-PrOH=4:1, 10 mL) and washed with sat. NH$_4$Cl. The organic layer was dried (anhydrous sodium sulfate) and concentrated in vacuo. The crude product was purified on silica gel chromatography (CH$_2$Cl$_2$/MeOH, 10:1) to yield the target compound 22 (165 mg, 66%). $^1$H NMR (CD$_3$OD, 400 MHz): δ 7.64 (d, J=8.4 Hz, 2H), 7.61 (d, J=3.6, 1H), 7.38 (m, 3H), 7.15 (m, 2H), 3.80 (m, 4H), 3.54 (s, 2H), 0.88 (s, 9H), 0.05 (s, 6H); $^{13}$C NMR (CD$_3$OD, 100 MHz): δ 171.0, 167.0, 142.6, 139.7, 130.8, 129.7, 128.8, 128.4, 127.6, 126.2, 60.7, 52.0, 41.0, 26.2, 18.0, −5.2; [M+H]$^+$=435.65 (APCI+).

N-hydroxy-5-(2-((2-hydroxyethyl)(phenyl)amino)-2-oxoethyl) thiophene-2-carboxamide (23)

Thiophene 22 (75 mg, 0.172 mmol) was dissolved in 2% HCl in MeOH (5 mL) and stirred for 3 h. Then the reaction mixture was concentrated in vacuo. The crude product was purified by preparative chromatography on silica gel (CH$_2$Cl$_2$/MeOH, 15:1) to yield target compound 23. (45 mg, 81%). $^1$H NMR (CD$_3$OD, 400 MHz): δ 7.64 (d, J=8.4 Hz, 2H), 7.61 (d, J=3.6, 1H), 7.38 (m, 3H), 7.15 (m, 2H), 3.86 (t, J=6.0 Hz, 2H), 3.68 (t, J=6.0 Hz, 2H), 3.55 (s, 2H); $^{13}$C NMR (CD$_3$OD, 100 MHz): δ 172.0, 166.9, 142.7, 139.7, 130.9, 129.9, 129.4, 128.7, 128.5, 127.1, 58.8, 51.8, 41.0; [M+H]$^+$=321.3 (APCI+).

Example 4. Synthesis of Compound 32

HDAC inhibitor 32 was prepared according to the protocols shown in Schemes 6 and 7. Amine 29 was coupled to acid 27 to form amide 30. The methyl ester of 30 was converted directly, using aqueous hydroxylamine, to the corresponding hydroxamic acid, which was deprotected with 2% aqueous HCl to afford compound 32.

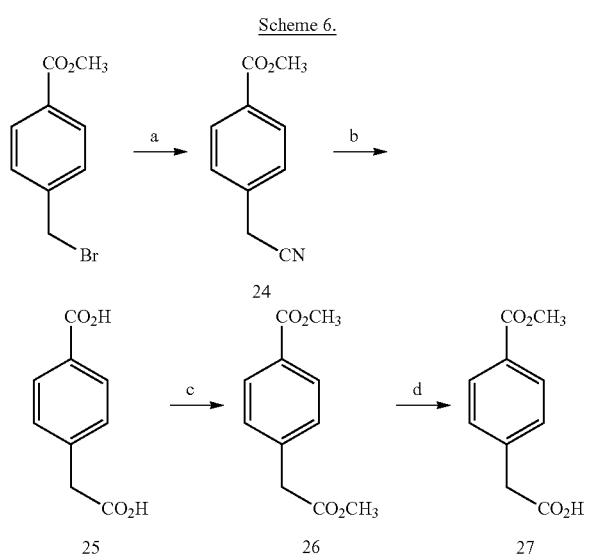

Reagents and conditions: a) NaCN, MeOH/H$_2$O, 70° C., 5 h; b) aq NaOH (6N), MeOH, 90° C. 12 h; c) MeOH/cat. H$_2$SO$_4$ 90° C. 18 h; d) MeOH, H$_2$O, K$_2$CO$_3$, rt, 12 h.

Methyl 4-(cyanomethyl)benzoate (24)

Commercially available 4-bromomethylbenzoic acid methyl ester (5.0 g) was dissolved in methanol (40 mL). A potassium cyanide solution (5.63 g in 8 mL water) was added dropwise over 15 min. The resulting suspension was heated to reflux for 5 h. Volatiles were removed under reduced pressure and the residue dissolved in diethylether and water. The organic layer was concentrated to a dark oil which was purified by column chromatography (5% ethyl acetate in hexane) to give the intermediate. Yield 3.82 g, 58.6%. [M+H]$^+$=176.3 (APCI+). $^1$H NMR (CHCl$_3$, 400 MHz): δ 8.05 (d, J=8.1 Hz, 1H), 7.42 (d, J=8.1 Hz, 1H), 3.93 (s, 3H), 3.81 (s, 2H).

4-(carboxymethyl)benzoic acid (25)

A solution of methyl 4-(cyanomethyl)benzoate 24, (2.0 g, 11.4 mmol) in 6M Sodium hydroxide (15 mL) and methanol (15 mL) was heated at 90° C. overnight. After concentrating the reaction mixture, the aqueous layer was washed with dichloromethane (30 mL×2), then acidified to pH~3 with 12M HCl. The aqueous solution was extracted with ethyl acetate (20 mL×2). Organics was combined, dried over Na$_2$SO$_4$ and evaporated in vacuo to give titled compound. (1.45 mg, 70%). [M+H]$^+$=181.4 (APCI+).

Methyl 4-(2-methoxy-2-oxoethyl)benzoate (26)

A solution of 4-(carboxymethyl)benzoic acid 25, (1.00 g, 5.55 mmol) and H$_2$SO$_4$ (2 mL) in methanol (20 mL) was heated at 90° C. overnight. After concentrating the reaction mixture, the crude was taken into EtOAc (30 mL) and washed with sat. NaHCO$_3$ (30 mL). Then the organic layer was dried over Na$_2$SO$_4$ and evaporated in vacuo. Crude material was purified on silica gel column (EtOAc:Hexanes=1:6) to give the title compound 26. (1.05 mg, 91%). $^1$H NMR (CHCl$_3$, 400 MHz): δ 8.00 (d, J=8.1 Hz, 1H), 7.37 (d, J=8.1, 1H), 3.90 (s, 3H), 3.69 (s, 3H), 3.67 (s, 2H); $^{13}$C NMR (CHCl$_3$, 100 MHz): δ 167.7, 138.8, 129.8, 129.3, 128.9, 52.5, 52.3, 41.2; [M+H]$^+$=209.3 (APCI+).

2-(4-(methoxycarbonyl)phenyl)acetic acid (27)

A solution of methyl 4-(2-methoxy-2-oxoethyl)benzoate 26, (800 mg, 3.85 mmol) and K$_2$CO$_3$ (929 mg, 5.67 mmol) in water/methanol mixture (20 mL, 1:1) was stirred at room temperature 4 hrs. After concentrating the reaction mixture to 5 mL diluted with water (20 mL). Then the aqueous layer was washed with dichloromethane (20 mL×2), and acidified to pH~3 with 12M HCl. The aqueous solution was extracted with ethyl acetate (20 mL×2). Organics was combined, dried over Na$_2$SO$_4$ and evaporated in vacuo to give titled compound 27. (620 mg, 83%). $^1$H NMR (CHCl$_3$, 400 MHz): δ 7.90 (d, J=8.1 Hz, 1H), 7.42 (d, J=8.1, 1H), 3.85 (s, 3H), 3.68 (s, 2H); [M+H]$^+$=195.4 (APCI+).

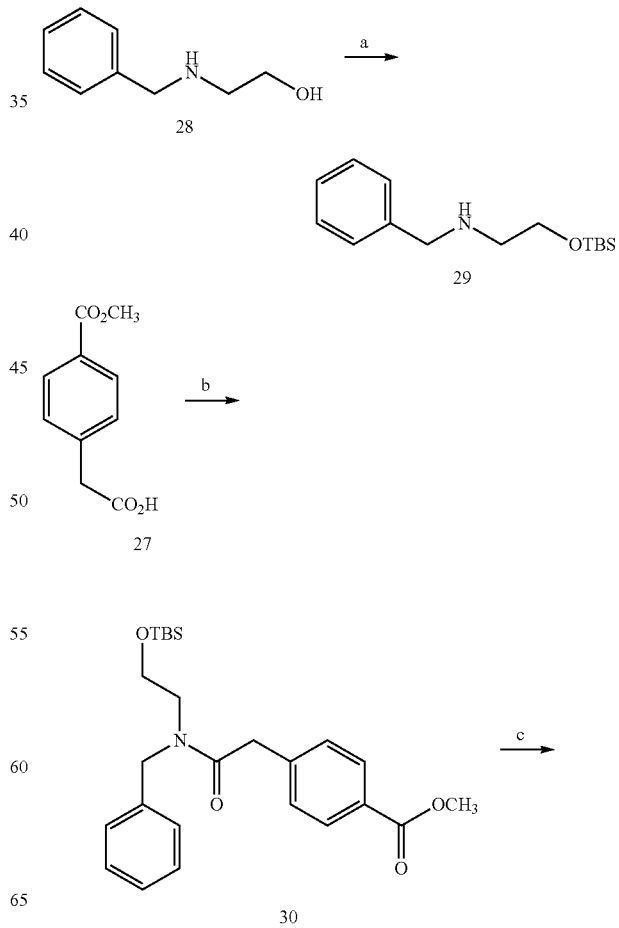

-continued

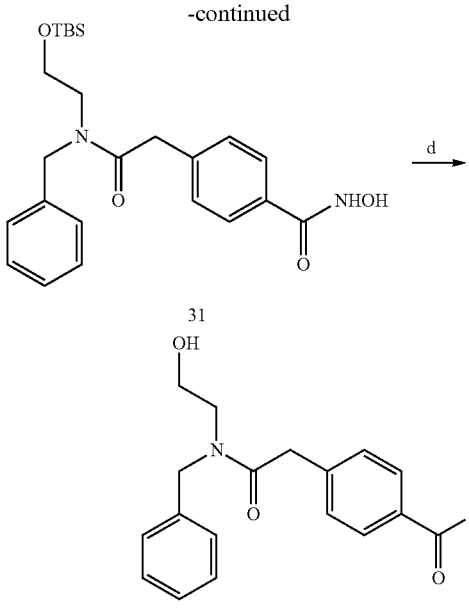

Reagents and conditions: a) Imidazole, TBSCl, CH₂Cl₂, 0° C. - rt; b) 29, EDCI, Et₃N, CH₂Cl₂, rt, 18 h; c) 50% (w/w) aq. NH₂OH, MeOH, rt; d) 2% aq. HCl, MeOH, 0° C. - rt.

N-benzyl.-2-((tart-butyldimethylsilyl)oxy)ethan-1-amine (29)

TBDMS-Cl (1.28 g, 8.02 mmol) and imidazole (1.45 g, 21.86 mmol) was added to a solution containing 2-(benzylamino)ethan-1-ol 1, (1.10 g, 7.29 mmol) in CH₂Cl₂ (10 mL). The reaction mixture was stirred at room temperature in argon atmosphere for 3 h. Then the reaction was quenched with sat. NH₄Cl, and washed with water (10 mL×2) and brine (10 mL×2). The organic layer was dried (anhydrous sodium sulfate) and concentrated in vacuo. The crude product was chromatographed on silica gel (Hexanes/EtOAc, 7:1) to yield target compound 29. Yield 1.59 g, 82%. [M+H]⁺=266.26 (APCI+).

Methyl 4-(2-(benzyl(2-((tert-butyldimethylsilyl)oxy) ethyl) amino)-2-oxoethyl)benzoate (30)

EDCI (582.0 mg, 3.4 mmol) was added to a solution containing N-benzyl-2-((tert-butyldimethylsilyl)oxy)ethan-1-amine 29, (848 mg, 3.2 mmol) and 2-(4-(methoxycarbonyl)phenyl)acetic acid 27, (504 mg, 2.6 mmol) in CH₂Cl₂ (5 mL). The reaction mixture was stirred overnight at room temperature in argon atmosphere. After completion of reaction the reaction mixture was diluted with mixed solvent (CHCl₃:i-PrOH=4:1, 10 mL) and washed with sat. NH₄Cl. The organic layer was dried (anhydrous sodium sulfate) and concentrated in vacuo. The crude product was chromatographed on silica gel (Hexanes/EtOAc, 7:1) to yield title compound 30. (820 mg, 58%). $^1$H NMR (CHCl₃, 400 MHz): δ 7.6 (d, J=8.1, Hz, 2H), 7.32 (m, 3H), 7.15 (m, 4H), 4.90 (s, 2H), 3.91 (s, 3H), 3.80 (m, 4H), 3.50 (s, 2H), 0.85 (s, 9H), 0.02 (s, 6H); [M+H]⁺=442.4 (APCI+).

4-(2-(benzyl(2-((tart-butyldimethylsilyl)oxy)ethyl) amino)-2-oxoethyl)-N-hydroxy-benzamide (31)

Hydroxylamine (0.5 mL, 50% water solution) was added to a solution containing methyl methyl 4-(2-(benzyl(2-((tert-butyldimethylsilyl)oxy)ethyl)amino)-2-oxoethyl)benzoate 30, (250 mg, 0.576 mmol) in THF/MeOH (1:1, 2 mL). Reaction mixture was treated with cat. amount of KCN (~0.5 mg) and stirred at room temperature in argon atmosphere for 16 h. Then solution was acidified by NH₄Cl/HCl solution to pH~4. The mixture was diluted with mixed solvent (CHCl₃:i-PrOH=4:1, 10 mL) and washed with sat. NH₄Cl. The organic layer was dried (anhydrous sodium sulfate) and concentrated in vacuo. The crude product was purified on silica gel chromatography (CH₂Cl₂/MeOH, 15:1) to yield the target compound 31 (130 mg, 52%). $^1$H NMR (CD₃OD, 400 MHz): δ 7.68 (d, J=8.4 Hz, 2H), 7.55 (m, 3H), 7.10 (d, J=8.0 Hz, 2H), 6.92 (d, J=8.0 Hz, 2H), 4.85 (s, 2H), 3.80 (m, 4H), 3.54 (s, 2H), 0.88 (s, 9H), 0.05 (s, 6H); [M+H]⁺=443.65 (APCI+).

4-(2-(benzyl(2-hydroxyethyl)amino)-2-oxoethyl)-N-hydroxy-benzamide (32)

4-(2-(benzyl(2-((tert-butyldimethylsilyl)oxy) ethyl) amino)-2-oxoethyl)-N-hydroxybenzamide, 31 (100 mg, 0.226 mmol) was dissolved in 2% HCl in MeOH (5 mL) and stirred for 3 h. Then the reaction mixture was concentrated in vacuo. The crude product was purified by preparative chromatography on silica gel (CH₂Cl₂/MeOH, 10:1) to yield target compound 32. (38 mg, 51%). $^1$H NMR (CD₃OD, 400 MHz): δ 7.64 (d, J=8.4 Hz, 2H), 7.45 (m, 3H), 7.29 (d, J=8.0 Hz, 2H), 7.14 (d, J=8.0 Hz, 2H), 3.86 (t, J=6.0 Hz, 2H), 3.68 (t, J=6.0 Hz, 2H), 3.55 (s, 2H); $^{13}$C NMR (CD₃OD, 100 MHz): δ 173.0, 167.9, 141.8, 139.2, 130.9, 129.9, 129.4, 128.7, 128.5, 127.1, 58.8, 51.8, 49.6, 41.0; [M+H]⁺; [M+H]⁺=329.3 (APCI+).

Example 5. Synthesis of Compound 36

HDAC inhibitor 36 was accessed according to the protocols shown in Scheme 8. Acid 33 was coupled to 4-(carboxymethyl)benzoic acid to form ester 34. The acid of compound 34 was coupled to O-protected hydroxylamine to form protected hydroxamate 35. Deprotection under acidic conditions gave inhibitor 36.

Scheme 8.

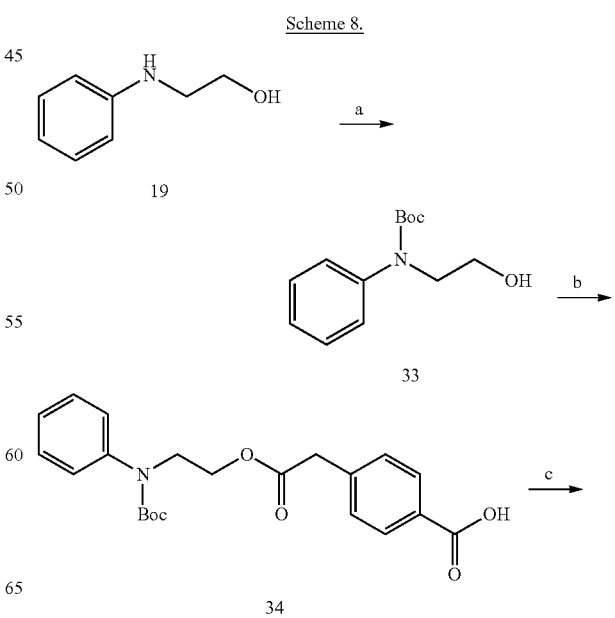

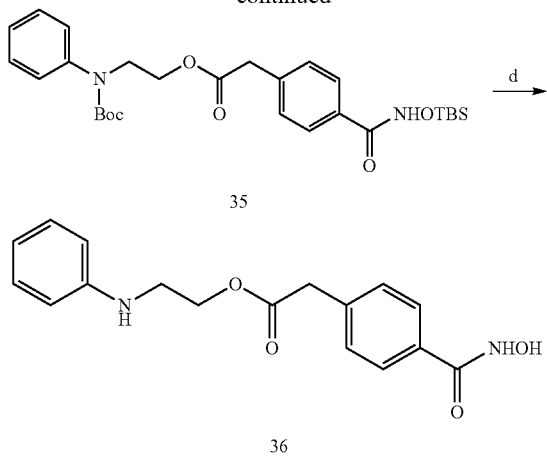

Reagents and conditions: a) Boc₂O, CH₂Cl₂, 0° C. - rt, 5 h; b) 4-(carboxymethyl) benzoic acid, EDCI, Et₃N, CH₂Cl₂, rt, 18 h; c) NH₂OTBS, EDCI, Et₃N, CH₂Cl₂, rt, 18 h; d) 2% aq. HCl, MeOH, 0° C. - rt.

tert-butyl (2-hydroxyethyl)(phenyl)carbamate (33)

2-Phenylamino-ethanol, 10 (2.5 g, 18 mmol) and di-t-butyl-dicarbonate (0.8 g, 1.5 eq.) in 25 mL of THF was heated to 55° C. for 7 h. Volatile was then removed in vacuo. The crude product was recrystallized from CH₂Cl₂ and hexane to give white crystalline material 33. (4 g, 65%). $^1$H NMR (CHCl₃, 400 MHz): δ 7.66 (d, J=8.0, 2H), 7.30 (m, 3H), 3.80 (s, 2H), 1.4 (s, 9H), 3.89 (s, 3H); [M+H]$^+$=238.4 (APCI+).

4-(2-(2-((tart-butoxycarbonyl)(phenyl)amino) ethoxy)-2-oxoethyl) benzoic acid (34)

EDCI (407.0 mg, 2.8 mmol) was added to a solution containing test-butyl (2-hydroxyethyl)(phenyl)carbamate 33, (660 mg, 2.8 mmol) and 4-(carboxymethyl)benzoic acid (468 mg, 2.6 mmol) in CH₂Cl₂ (5 ml). The reaction mixture was stirred for 5 hrs at room temperature in argon atmosphere. After completion of reaction the reaction mixture was diluted with sat. NH₄Cl and extracted with EtOAc (30 mL×3). The organic layer was dried (anhydrous sodium sulfate) and concentrated in vacuo. The crude product was chromatographed on silica gel (Hexanes/EtOAc, 7:1) to yield title compound 34. (610 mg, 60%). [M+H]$^+$=400.2 (APCI+).

2-((tert-butoxycarbonyl)(phenyl)amino)ethyl-2-(4-(((tert-butyl-dimethylsilyl)oxy) carbamoyl)phenyl) acetate (35)

EDCI (203 mg, 1.4 mmol) was added to a solution containing O-(tert-butyldimethylsilyl) hydroxylamine, (162 mg, 1.1 mmol) in CH₂Cl₂ (5 mL). The reaction mixture was stirred for 18 hrs at room temperature in argon atmosphere. After completion of reaction the reaction mixture was diluted with with sat. NH₄Cl and extracted with EtOAc (30 mL×3). The organic layer was dried (anhydrous sodium sulfate) and concentrated in vacuo. The crude product was chromatographed on silica gel (Hexanes/EtOAc, 7:1) to yield title compound 35. (275 mg, 47%). [M+H]$^+$=529.5 (APCI+).

2-(phenylamino)ethyl 2-(4-(hydroxycarbamoyl)phenyl)acetate (36)

2-((tert-butoxycarbonyl)(phenyl)amino)ethyl 2-(4-(((tert-butyl-dimethylsilyl)oxy)carbamoyl) phenyl) acetate 35 (100 mg, 0.189 mmol) was dissolved in 2% HCl in MeOH (5 mL) and stirred for 3 h. Then the reaction mixture was concentrated in vacuo. The crude product was purified by preparative chromatography on silica gel (CH₂Cl₂/MeOH, 10:1) to yield target compound 36. (28 mg, 47%). $^1$H NMR (CD₃OD, 400 MHz): δ 7.71 (d, J=8.4 Hz, 2H), 7.38 (d, J=8.4 Hz, 2H), 7.12 (t, J=8.0, Hz 3H), 6.65 (m, 3H), 4.27 (t, J=6.0 Hz, 2H), 3.73 (s, 2H), 3.39 (t, J=6.0 Hz, 2H); $^{13}$C NMR (CD₃OD, 100 MHz): δ 171.5, 166.5, 148.3, 138.2, 130.9, 129.3, 129.4, 128.7, 126.9, 116.9, 112, 7, 63.5, 42.1, 40.2; [M+H]$^+$ 314.38 (APCI+).

Example 6. Cell Assay of Compounds 8 and 11

Figure 2:
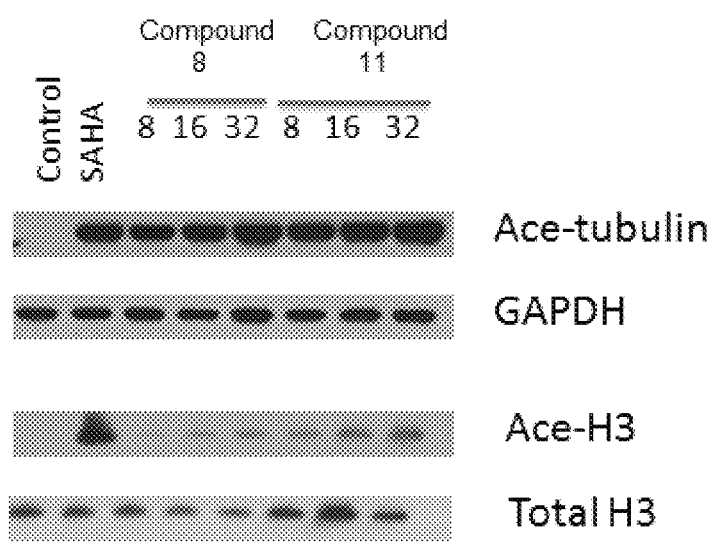
FIG. 2. Blot showing accumulation of acetylated alpha-tubulin and acetylated histone H3 in LNCaP (human prostate cancer cells) cultured with compounds 8 or 11. GADPH used as loading control.

As shown in the cell based (LNCaP-human prostate) assay (FIG. 2), compounds 8 and 11 caused the accumulation of acetylated α-tubulin, a substrate of HDAC6. However, compounds 8 and 11 did not cause accumulation of acetylated histones, which is not a substrate of HDAC6, indicating HDAC6 selectivity.

Example 7. HDAC6 vs. HDAC1 Activity

Compounds 8 and 11 were assayed for inhibition of recombinant HDAC6 and HDAC1 (Table 1). Compound 8 has an IC₅₀ inhibitory activity for HDAC6 of 31 nM compared with 1128 nM for HDAC1 (ratio HDAC1:HDAC6=36.38). Compound 11 has an IC₅₀ inhibitory activity for HDAC6 of 11 nM compared with 270 nM for HDAC1 (ratio HDAC1:HDAC6=24.54).

Compound 8 is one hundred fold more potent inhibitor of HDAC6 than SAHA (suberoylanilide hydroxamic acid). Compound 8 is assayed against eleven zinc containing HDACS and is 15 to almost 400 fold more potent inhibitor of HDAC6 than other zinc dependent HDAC's.

TABLE 1

| Compound | IC₅₀ (nM) HCAC1 | IC₅₀ (nM) HCAC6 | Ratio: HDAC1/HDAC6 |
|---|---|---|---|
| 8 | 1128 | 31 | 36.38 |
| 11 | 270 | 11 | 24.54 |
| SAHA | 54 | 21 | 3.09 |
| Tubacin | 193 | 45 | 4.3 |

Example 8. Cell Growth vs. Cell Viability

Figure 3:
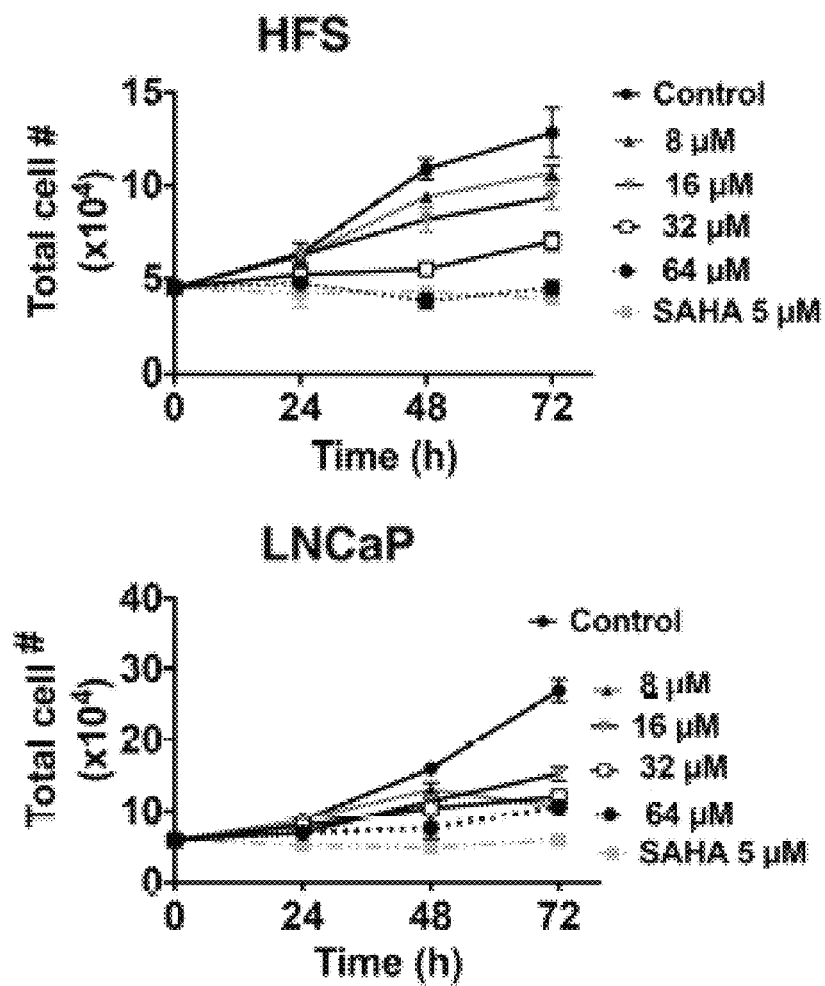
FIG. 3. Cell growth of HFS (normal) and LNCaP (transformed) cells treated with compound 8 over 72 h.
Figure 4:
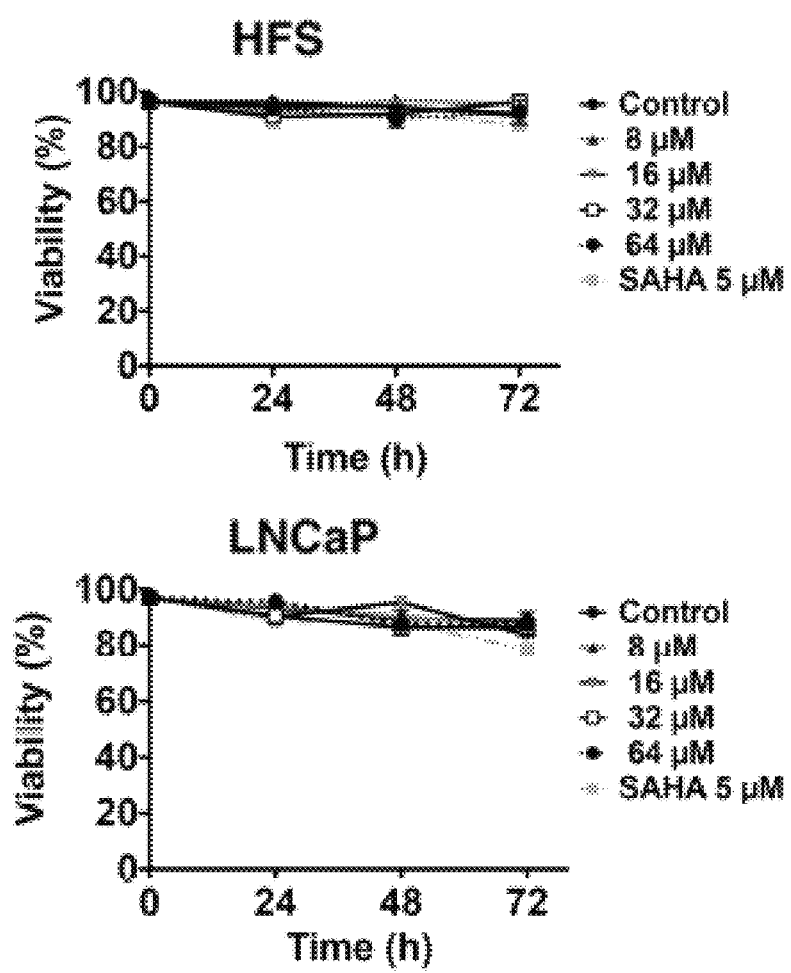
FIG. 4. Cell viability of HFS (normal) and LNCaP (transformed) cells treated with compound 8 over 72 h.

The effect of compound 8 on the cell growth and viability of normal (HFS, human foreskin fibroblast) and transformed (LNCaP, human prostate adenocarcinoma) cells cultured with 8, 16, 32 or 64 μM HPB for up to 72 h was evaluated. Compound 8 inhibited cell growth of normal and transformed cells in a concentration dependent manner (FIG. 3), but did not induce cell death of normal or transformed cells (FIG. 4).

Example 9. Acetylation of Alpha-Tubulin vs. Histones

Figure 5:
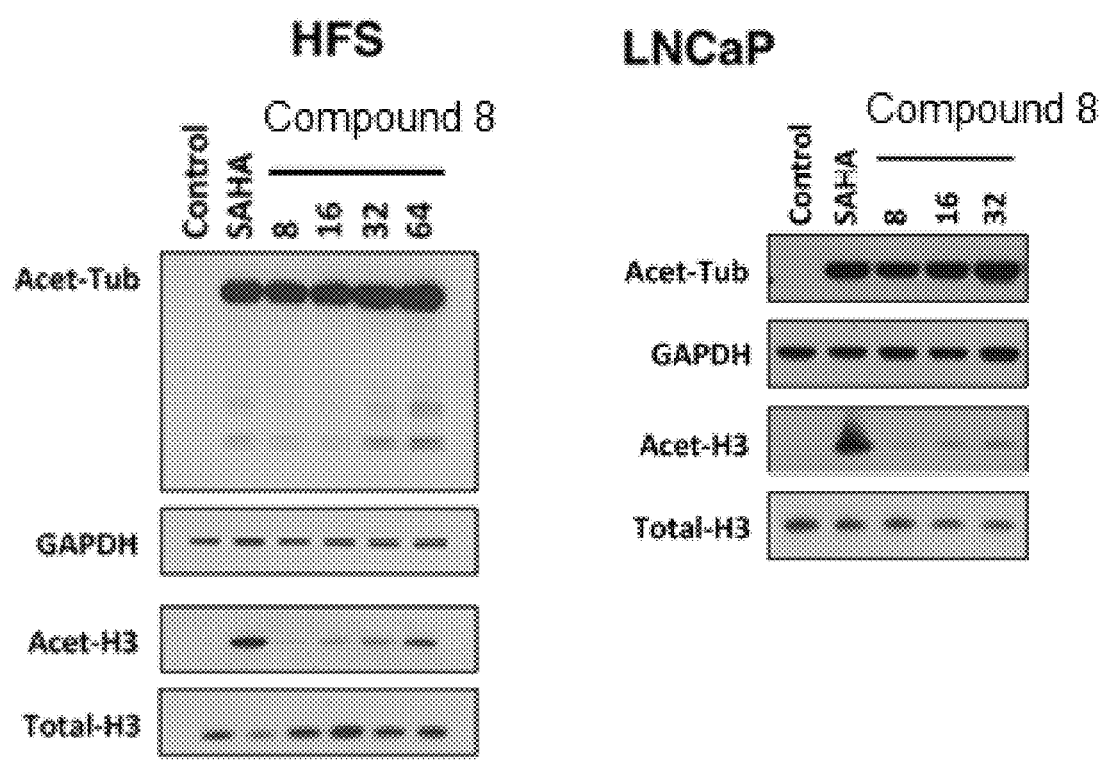
FIG. 5. Western blots of acetylated alpha-tubulin (Acet-Tub) and acetylated histone H3 (Acet-H3) in HFS (normal) and LNCaP (transformed) cells treated with compound 8 at 8, 16, 32, and 64 µM for 24 h. Western blots of GAPDH and total histone H3 (Total-H3) are loading controls.

In normal (HFS) and transformed (LNCAP) cells, compound 8, at 8 μM to 64 μM, caused accumulation of acetylated alpha-tubulin, a substrate of HDAC6 (Kovacs J J, et al. 2005; Parmigiani R B, et al. 2008), but not of acetylated histones (FIG. 5). SAHA induced the accumulation of acetylated alpha-tubulin and histone H3 (Marks, P. et al. 2007; Lee et al. 2010; Namdar et al. 2010).

Example 10. Mouse Toxicity Studies

Figure 6:
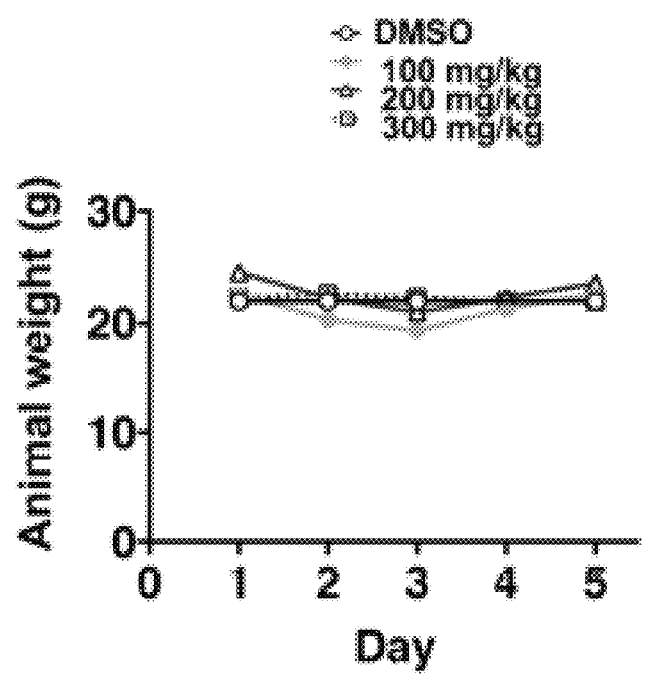
FIG. 6. Average weight of immune-deficient mice treated daily by 30 µL intraperitoneal injection with indicated doses of compound 8. DMSO is the vehicle control.
Figure 7:
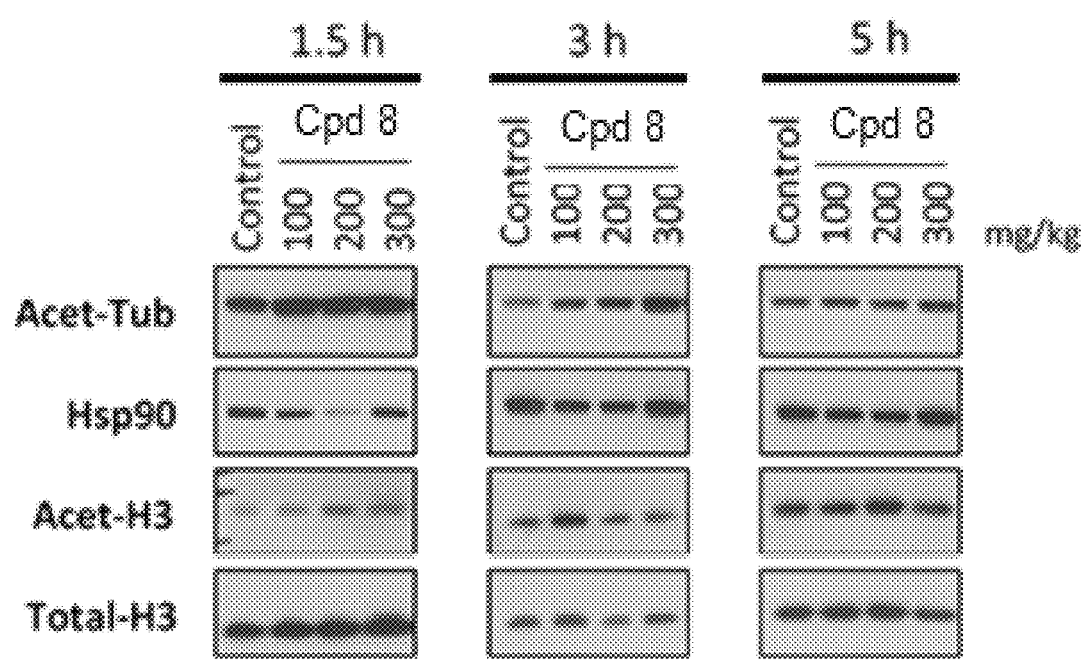
FIG. 7. Immunoblots of spleens harvested at indicated times after the last injection. Immune-deficient mice were treated daily by 30 µL intraperitoneal injection with indicated doses of compound 8. DMSO is the vehicle control. Western blots of acetylated alpha-tubulin (Acet-Tub) and acetylated histone H3 (Acet-H3). Western blots of HSP90 and total histone H3 (Total-H3) are loading controls.

Toxicity of compound 8 in mice was determined. Compound 8 is well tolerated in animals. Mice were intraperitoneally injected daily for 5 days with 100, 200, or 300 mg/kg compound 8. There was no weight loss in the mice (FIG. 6). The effects of compound 8 on the acetylation of alpha-tubulin and histones in the spleen isolated from mice treated with compound 8 were analyzed at three time points after the administration of the drug. At 1.5 h after injection of compound 8, an increased accumulation of acetylated tubulin was found in the spleen (FIG. 7). By 5 h after injection of compound 8, the accumulation of acetylated tubulin was reduced to the level seen in vehicle-treated controls. There was no detectable accumulation of acetylated histones in the spleen from the mice receiving the compound (FIG. 7).

Example 11. Combination of Compound 8 with Anti-Cancer Agents

It has been reported that inhibition of HDAC6 by either si-RNA or tubacin potentiates the cytotoxicity of anti-cancer drugs in transformed but not normal cells (Namdar et al. 2010; Lee et al. 2013). To assess whether selective inhibition of HDAC6 by compound 8 enhances cell death of normal and transformed cells in culture with anticancer agents, cells are cultured with compound 8 and the topoisomerase II inhibitor, etoposide, or the mitotic inhibitor, paclitaxel, or the pan-HDAC inhibitor, SAHA, for 72 h.

In HFS (normal) cells, compound 8 alone or in combination with etoposide, paclitaxel, or SAHA inhibits cell growth but does not induce loss of cell viability.

LNCaP (transformed) cells cultured with 50 µM etoposide and 16 µM compound 8 demonstrates inhibition in cell growth and loss of cell viability to a greater extent than LNCaP cells cultured with etoposide alone. LNCaP cell death is enhanced in cultures with compound 8 and 5 µM SAHA compared with cultures with SAHA alone. Combined treatment with paclitaxel and compound 8 caused increases cell death in LNCaP cells compared to either drug alone.

Example 12. Mouse Studies with Combination of Compound 8 with Anti-Cancer Drugs

The effects of compound 8 in combination with the anti-cancer drug, etoposide, are examined in nude mice implanted with the androgen-dependent CWR22 human prostate cancer xenograft, which was grown subcutaneously. Daily administration of either 300 mg/kg compound 8 or weekly administration of 3 mg/kg etoposide alone for 21 days causes no significant suppression of the growth of established CWR22 tumors and no weight loss. Daily administration of compound 8 and weekly administration of etoposide causes suppression of the growth of established CWR22 tumors, such that doses cause reductions in the mean final tumor volume compared with vehicle-treated control animals. Tumors and spleen are removed from the animals, and histones and proteins are extracted for the detection of acetylated lysine patterns. There is increased accumulation of acetylated alpha-tubulin in CWR22 tumors and spleen from mice treated with compound 8, etoposide, or combination of compound 8 and etoposide (FIG. 6D). Increased levels of accumulation of histones are found in tumors of mice injected with etoposide or combination of etoposide and compound 8, but not with compound 8 alone. This data indicates that compound 8 is a selective inhibitor of HDAC6 in vivo and enhances anti-tumor effect of a chemotherapeutic agent.

Example 13. Additional Selective HDAC6 Inhibitors

The compounds of the present invention are HDAC6 selective inhibitors. An additional aspect of the invention provides synthetic methods and chemical intermediates that may be used to synthesize additional HDAC6 inhibitors. Additional compounds, which are synthesized according to methods similar to those described in Schemes 1-8 or according to methods known in the art, have analogous activity to compounds 8 and/or 11. The left hand portion of the compound (Rd is also varied to improve solubility and drug-like properties and compounds with various $R_1$ groups function analogously to compounds 8 and/or 11.

Example 14. Administration of Compound 8 or 11

An amount of compound 8 or 11 is administered to a subject afflicted with a neurodegenerative disease, cancer, or HIV infection. The amount of the compound is effective to treat the subject.

An amount of compound 8 or 11 in combination with an anti-cancer agent is administered to a subject afflicted with cancer. The amount of the compound is effective to enhance the anti-cancer activity of the anti-cancer agent.

An amount of compound 8 or 11 in combination with etoposide, paclitaxel, or SAHA, is administered to a subject afflicted with cancer. The amount of the compound is effective to enhance the anti-cancer activity of the etoposide, paclitaxel, or SAHA.

An amount of an analogue of compound 8 or 11 is administered to a subject afflicted with a neurodegenerative disease, cancer, or HIV infection. The amount of the analogue is effective to treat the subject.

An amount of an analogue of compound 8 or 11, in combination with an anti-cancer agent is administered to a subject afflicted with cancer. The amount of the analogue is effective to enhance the anti-cancer activity of the anti-cancer agent.

An amount of an analogue of compound 8 or 11 in combination with etoposide, paclitaxel, or SAHA is administered to a subject afflicted with cancer. The amount of the analogue is effective to enhance the anti-cancer activity of the etoposide, paclitaxel, or SAHA.

Discussion

There are eleven zinc dependent histone deacetylase (HDAC) in humans. All HDAC's are nuclear proteins except for HDAC6. HDAC6 is unique among HDACs in being a cytoplasmic protein with two catalytic sites and an ubiquitin binding site. HDAC6 substrates include a number of proteins, eg. tubulin, peroxidases, certain DNA repair proteins, but not histones. HDAC6 has a role in the cellular response to accumulation of misfolded and aggregated proteins which are catalysts of certain neurological disconnects such as Alzheimer's, Parkinson's, and Huntington's diseases.

HDAC6-selective inhibitors were identified on the basis of accumulation of acetylated tubulin without accumulation of acetylated histones. Compound 8 and 11 were identified as HDAC6-selective inhibitors. As show in FIG. 2, significant levels of tubulin acylation were present without induction of H3 acetylation.

As indicated by the cell based (LNCaP-human prostate) assays, compounds 8 inhibited cell number but does not decrease cell viability. Unlike SAHA, which kills LNCaP cells, there is no detectable death of LNCaP cells with compound 8 even at concentrations as high as 32 µM.

Compound 8 inhibited HDAC6 in vitro with approximately 36-fold selectivity against HDAC6 over HDAC1 enzyme. Concentrations as high as 16 µM of compound 8 selectively induced accumulation of acetylated alpha-tubulin and acetylated PRX, substrates of HDAC6, but not of acetylated histones in both normal and transformed cells. Histones are not a substrate of HDAC6. Compound 8 in concentrations ≤16 µM do not induce normal cell death.

Culture of transformed cells with compound 8 enhances the cytotoxicity of anti-cancer drugs through increased induction of apoptosis and accumulation of DNA damage. Compound 8 also enhances etoposide or SAHA-induced transformed cell death. Compound 8 in combination with etoposide significantly enhances the anti-tumor effect of etoposide in nude mice with androgen-dependent CWR22 human prostate cancer xenograft.

These findings indicate that selective inhibition of HDAC6 in combination with anti-cancer drugs may be an important avenue to enhance therapeutic efficacy of such drugs in treating human cancers.

REFERENCES

P. Bali; M. Pranpat; J. Bradner; M. Balasis; W. Fiskus; F. Guo; K. Rocha; S. Kumaraswamy; S. Boyapalle; P. Atadja; E. Seto; K. Bhalla. "Inhibition of Histone Deacetylase 6 Acetylates and Disrupts the Chaperone Function of Heat Shock Protein 90" *J. Biol. Chem.* (2005), 280, 26729-26734.

K. V. Butler and A. P. Kozikowski "Chemical Origins of Isoform Selectivity in Histone Deacetylase Inhibitors" *Curr. Pharma. Design* (2008), 14, 505-528.

Y.-S. Gap; C. C. Hubbert; T.-P. Yao. "The Microtubule-associated Histone Deacetylase 6 (HDAC6) Regulates Epidermal Growth Factor Receptor (EGFR) Endocytic Trafficking and Degradation" *J. Biol. Chem.* (2010), 285, 11219-11226.

S. J. Haggarty; K. M. Koeller; J. C. Wong; C. M. Grozinger; S. L. Schreiber. "Domain-selective small-molecule inhibitor of histone deacetylase 6 (HDAC6)-mediated tubulin deacetylation" *Proc. Nat. Sci. Acad. USA* (2003), 100, 4389-4394.

Y. Kawaguchi; J. J. Kovacs; A. McLaurin; J. M. Vance; A. Ito; T.-P. Yao "The Deacetylase HDAC6 Regulates Aggresome Formation and Cell Viability in Response to Misfolded Protein Stress" *Cell* (2003), 115, 727-738.

J. J. Kovacs; P. J. M. Murphy; S. Gaillard; X. Zhao; T. Wu; C. V. Nicchitta; M. Yoshida; D. O. Toft; W. B. Pratt; T.-P. Yao. "HDAC6 Regulates Hsp90 Acetylation and Chaperone-Dependent Activation of Glucocorticoid Receptor" *Molecular Cell* (2005) 18, 601-607.

Lee, J. H. et al. "Histone deacetylase inhibitor induces DNA damage, which normal but not transformed cells can repair" (2010) Proc Natl Aced Sci USA, 107, 14639-14644

Lee, J-H et al. "Development of a histone deacetylase 6 inhibitor and its biological effects (2013) Proc Natl Acad Sci USA, 110, 15704-15709, 14639-14644.

Marks, P. S., Breslow, R. Dimethyl sulfoxide to vorinostat: development of this histone deacetylase inhibitor as an anti-cancer drug. *Nat. Biotech.* (2007) 25, 84-90.

Marks, P. A. Histone Deacetylase Inhibitors: A chemical genetics approach to understanding cellular functions, *Biochimica et. Biophysicia Acta* (2010) 1799 (10-12), 717-725.

Munkacsi, Andrew B. et al., "An "exacerbate-reverse" strategy in yeast identifies histone deacetylase inhibition as a correction for cholesterol and sphingolipid transport defects in human niemann-pick type C disease", *J. Biol. Chem.* (2011) 286, 23842-23851.

Namdar et al. "Selective inhibition of histone deacetylase 6 (HDAC6) induces DNA damage and sensitizes transformed cells to anticancer agents" (2010) PNAS, 107, 20003-8.

R. B. Parmigiani, W. S. Xu, G. Venta-Perez, H. Brdjument-Bromage, M. Yaneva, P. Tempst, and P. A. Marks. "HDAC6 is a specific deacetylase of peroxiredoxins and is involved in redox regulation" *Proc. Nat. Acad. Sci. USA* (2008), 105, 9633-9638.

What is claimed is:

1. A compound having the structure:

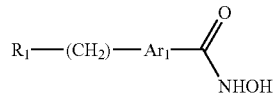

wherein
R$_1$ is —NR$_5$—C(=O)—R$_6$ or —C(=O)—NR$_5$R$_6$,
wherein R$_5$ and R$_6$ are each, independently, hydroxyalkyl, aryl, heteroaryl or C$_{1-5}$ alkyl-aryl;
Ar$_1$ is phenyl;
wherein when Ar$_1$ is phenyl, then R$_1$ is other than —C(=O)—NR$_5$R$_6$, where one of R$_5$ or R$_6$ is phenyl or quinoline and the other of R$_5$ or R$_6$ is —CH$_2$CH$_2$OH,
or a pharmaceutically acceptable salt thereof.

2. The compound of claim 1,
wherein
Ar$_1$ is

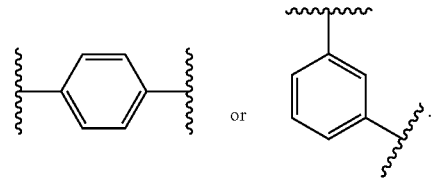 [SMILES: *c1ccc(*)cc1 ; *c1cccc(*)c1]

3. The compound of claim 1,
wherein
R$_1$ is —C(=O)—NR$_5$R$_6$ or —NR$_5$—C(=O)—R$_6$,
wherein
R$_5$ is C$_{1-5}$ alkyl-aryl or hydroxyalkyl; and
R$_6$ is C$_{1-5}$ alkyl-aryl or hydroxyalkyl.

4. The compound of claim 1,
wherein
R$_1$ is —C(=O)—NR$_5$R$_6$ or —NR$_5$—C(=O)—R$_6$,
wherein R$_5$ and R$_6$ are each, independently, phenyl, —CH$_2$CH$_2$OH or —CH$_2$-phenyl.

5. The compound of claim 4,
wherein
R$_1$ is —C(═O)—NR$_5$R$_6$ or —NR$_5$—C(═O)—R$_6$,
    wherein R$_5$ and R$_6$ are each, independently,

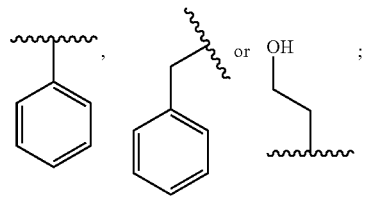

or
R$_1$ is —C(═O)—NR$_5$R$_6$,
    wherein R$_5$ is

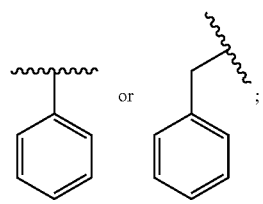 [SMILES: *c1ccccc1 ; *Cc1ccccc1]

and R$_6$ is

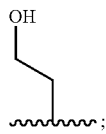

or
R$_1$ is —NR$_5$—C(═O)—R$_6$,
    wherein R$_5$ is

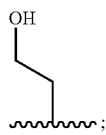 [SMILES: *CCO]

and R$_6$ is

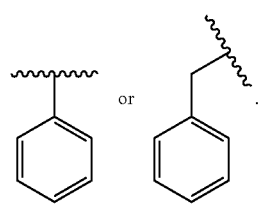 [SMILES: *c1ccccc1 ; *Cc1ccccc1]

6. The compound of claim 1 having the structure:

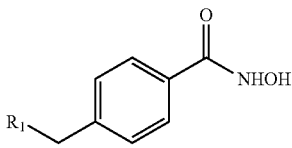

wherein
R$_1$ is —NR$_5$—C(═O)—R$_6$ or —C(═O)—NR$_5$R$_6$,
    wherein R$_5$ and R$_6$ are each, independently, aryl, heteroaryl or C$_{1-5}$ alkyl-aryl;
    wherein R$_1$ is other than —C(═O)—NR$_5$R$_6$, where one of R$_5$ or R$_6$ is phenyl or quinoline and the other of R$_5$ or R$_6$ is —CH$_2$CH$_2$OH,
or a pharmaceutically acceptable salt thereof.

7. The compound of claim 1,
wherein
R$_1$ is —C(═O)—NR$_5$R$_6$ or —NR$_5$—C(═O)—R$_6$,
    wherein
    R$_5$ is hydroxyalkyl or aryl;
    R$_6$ is hydroxyalkyl or aryl,
or a pharmaceutically acceptable salt thereof.

8. The compound of claim 1 having the structure:

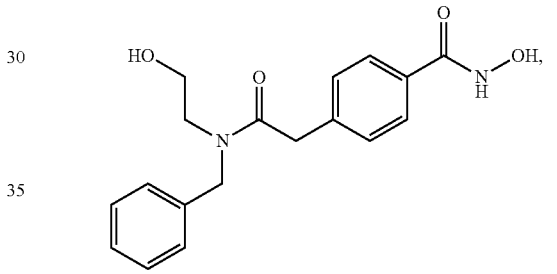

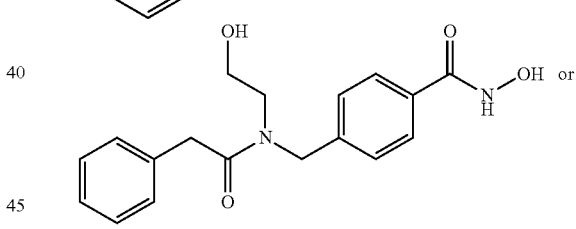

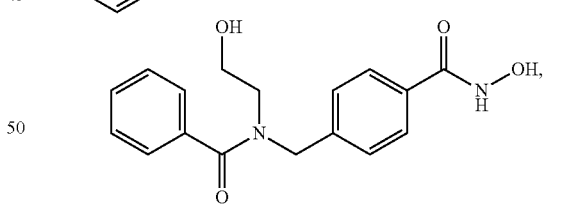

or a pharmaceutically acceptable salt thereof.

9. A pharmaceutical composition comprising the compound of claim 1 and a pharmaceutically acceptable carrier.

10. A method of inhibiting the activity of a histone deactylase in a cell comprising contacting the histone deacetylase with the compound of claim 1 so as to inhibit the activity of the histone deacetylase.

11. The method of claim 10, wherein the histone deacetylase is HDAC6.

12. A method of treating cancer in a subject afflicted therewith comprising administering an effective amount of the compound of claim 1 to the subject so as to treat the cancer in the subject.

13. A method of treating a subject afflicted with cancer comprising periodically administering to the subject
   a) an amount of the compound of claim 1 or a pharmaceutically acceptable salt thereof, and
   b) an anti-cancer agent.

14. The method of claim 13, wherein the anti-cancer agent is selected from x-radiation, ionizing radiation, a DNA damaging agent, a DNA intercalating agent, a microtubule stabilizing agent, a microtubule destabilizing agent, a spindle toxin, abarelix, aldesleukin, alemtuzumab, alitertinoin, allopurinol, altretamine, amifostin, anakinra, anastrozole, arsenic trioxide, asparaginase, azacitidine, bevacizumab, bexarotene, bleomycin, bortezomib, busulfan, calusterone, capecitabine, carboplatin, carmustine, celecoxib, cetuximab, chlorambucil, cisplatin, cladribine, clofarabine, cyclophosphamide, cytarabine, dacarbazine, dactinomycin, actinomycin D, dalteparin sodium, darbepoetin alfa, dasatinib, daunorubicin, daunomycin, decitabine, denileukin, dexrazoxane, docetaxel, doxorubicin, dromostanolone propionate, exulizumab, epirubicin, epoetin alfa, erlotinib, estramustine, etoposide phosphate, etoposide, VP-16, exemestane, fentanyl citrate, filgrastim, floxuridine, fludarabine, fluorouracil, fulvestrant, gefitinib, gemcitabine, gosereline acetate, histrelin acetate, hydroxyurea, ibritumomab tiuxetan, idarubicin, ifosfamide, imatinib mesylate, interferon alfa 2a, interferon alfa 2b, irinotecan, lapatinib ditosylate, lenalidomide, letrozole, leucovrin, leuprolide acetate, levamisole, lomustine, meclorethamine, megestrol acetate, melphalan, mercaptopurine, mesna, methotrexate, methoxsalen, mitomycin C, mitotane, mitoxantrone, nandrolone phenpropionate, nelarabine, nofetumomab, oprelvekin, oxaliplatin, paclitaxel, palifermin, pamidronate, panitumumab, pegademase, pegaspargase, pegfilgrastim, peginterferon alfa 2b, pemetrexed disodium, pentostatin, pipobroman, plicamycin, mithramycin, porfimer sodium, procarbazine, quinacrine, rasburicase, rituximab, SAHA, sargrmostim, sorafenib, streptozocin, sunitinib, sunitinib maleate, talc, tamoxifen, temozolomide, teniposide, VM-26, testolactone, thalidomide, thioguanine, G-TG, thiotepa, topotecan, toremifene, tositumomab, trastuzumab, tretinoin ATRA, uracil mustard, valrunicin, vinblastine, vincristine, vinorelbine, vorinostat, zoledronate, zoledronic acid, protein-bound paclitaxel or brentuximab vedotin.

15. The compound of claim 1 having the structure:

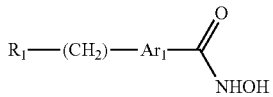

wherein
R$_1$ is —NR$_5$—C(=O)—R$_6$ or —C(=O)—NR$_5$R$_6$,
   wherein R$_5$ and R$_6$ are each, independently, hydroxyalkyl or C$_{1-5}$ alkyl-aryl;
Ar$_1$ is phenyl;
or a pharmaceutically acceptable salt thereof.

16. The compound of claim 1 having the structure:

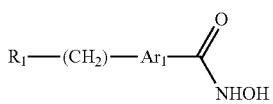

wherein
R$_1$ is —NR$_5$—C(=O)—R$_6$,
   wherein R$_5$ and R$_6$ are each, independently, hydroxyalkyl or C$_{1-5}$ alkyl-aryl;
Ar$_1$ is phenyl;
or a pharmaceutically acceptable salt thereof.

17. The compound of claim 1 having the structure:

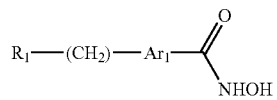

wherein
R$_1$ is —NR$_5$—C(=O)—R$_6$,
   wherein R$_5$ and R$_6$ are each, independently, hydroxyalkyl or aryl;
Ar$_1$ is phenyl;
or a pharmaceutically acceptable salt thereof.

18. The compound of claim 1 having the structure:

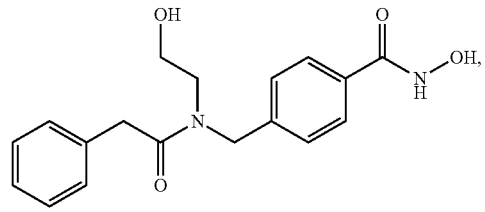 [SMILES: O=C(NO)c1ccc(CN(CCO)C(=O)Cc2ccccc2)cc1]

or a pharmaceutically acceptable salt thereof.

19. A pharmaceutical composition comprising the compound of claim 18 and a pharmaceutically acceptable carrier.

20. A method of treating cancer in a subject afflicted therewith comprising administering an effective amount of the compound of claim 18 to the subject so as to treat the cancer in the subject.

21. A method of treating a subject afflicted with cancer comprising periodically administering to the subject
   a) an amount of the compound of claim 18 or a pharmaceutically acceptable salt thereof, and
   b) an anti-cancer agent.

22. The method of claim 21, wherein the anti-cancer agent is selected from x-radiation, ionizing radiation, a DNA damaging agent, a DNA intercalating agent, a microtubule stabilizing agent, a microtubule destabilizing agent, a spindle toxin, abarelix, aldesleukin, alemtuzumab, alitertinoin, allopurinol, altretamine, amifostin, anakinra, anastrozole, arsenic trioxide, asparaginase, azacitidine, bevacizumab, bexarotene, bleomycin, bortezomib, busulfan, calusterone, capecitabine, carboplatin, carmustine, celecoxib, cetuximab, chlorambucil, cisplatin, cladribine, clofarabine, cyclophosphamide, cytarabine, dacarbazine, dactinomycin, actinomycin D, dalteparin sodium, darbepoetin alfa, dasatinib, daunorubicin, daunomycin, decitabine, denileukin, dexrazoxane, docetaxel, doxorubicin, dromostanolone propionate, exulizumab, epirubicin, epoetin alfa, erlotinib, estramustine, etoposide phosphate, etoposide, VP-16, exemestane, fentanyl citrate, filgrastim, floxuridine, fludarabine, fluorouracil, fulvestrant, gefitinib, gemcitabine, gosereline acetate, histrelin acetate, hydroxyurea, ibritumomab tiuxetan, idarubicin, ifosfamide, imatinib mesylate, interferon alfa 2a, interferon alfa 2b, irinotecan, lapatinib ditosylate, lenalidomide, letrozole, leucovrin, leuprolide acetate, levamisole, lomustine, meclorethamine, megestrol acetate, melphalan, mercaptopurine, mesna, methotrexate, methoxsalen, mitomycin C, mitotane, mitoxantrone, nandrolone phenpropionate, nelarabine, nofetumomab, oprelvekin, oxaliplatin, paclitaxel, palifermin, pamidronate, panitumumab, pegademase, pegaspargase, pegfilgrastim, peginterferon alfa 2b, pemetrexed disodium, pentostatin, pipobroman, plicamycin, mithramycin, porfimer sodium, procarbazine, quinacrine, rasburicase, rituximab, SAHA, sargrmostim, sorafenib, streptozocin, sunitinib, sunitinib maleate, talc, tamoxifen, temozolomide, teniposide, VM-26, testolactone, thalidomide, thioguanine, G-TG, thiotepa, topotecan, toremifene, tositumomab, trastuzumab, tretinoin ATRA, uracil mustard, valrunicin, vinblastine, vincristine, vinorelbine, vorinostat, zoledronate, zoledronic acid, protein-bound paclitaxel or brentuximab vedotin.

\* \* \* \* \*